(12) United States Patent
Petersen

(10) Patent No.: US 7,407,496 B2
(45) Date of Patent: Aug. 5, 2008

(54) FASTENING FILM SYSTEM AND ASSEMBLY COMPRISING A FASTENING FILM SYSTEM AND A SUBSTRATE

(75) Inventor: Johann F. Petersen, Grevenbroich (DE)

(73) Assignee: 3M Innovative Properties Company, St. Paul, MN (US)

( * ) Notice: Subject to any disclaimer, the term of this patent is extended or adjusted under 35 U.S.C. 154(b) by 233 days.

(21) Appl. No.: 10/557,092

(22) PCT Filed: May 10, 2004

(86) PCT No.: PCT/US2004/014620

§ 371 (c)(1),
(2), (4) Date: Nov. 17, 2005

(87) PCT Pub. No.: WO2005/000181

PCT Pub. Date: Jan. 6, 2005

(65) Prior Publication Data

US 2006/0293635 A1    Dec. 28, 2006

(30) Foreign Application Priority Data

Jun. 6, 2003    (EP) .................................. 03012951

(51) Int. Cl.
*A44B 18/00* (2006.01)

(52) U.S. Cl. .................. 604/390; 428/99; 428/100; 428/137; 428/343; 428/354; 24/304; 24/306; 24/442; 24/450; 24/452

(58) Field of Classification Search ............. 604/386, 604/389, 385.13, 391; 428/99, 100, 137, 428/343, 354; 24/304, 306, 442, 450, 452
See application file for complete search history.

(56) References Cited

U.S. PATENT DOCUMENTS

| | | |
|---|---|---|
| 3,937,221 A | 2/1976 | Tritsch |
| 4,001,366 A | 1/1977 | Brumlik |
| 4,067,337 A | 1/1978 | Ness |
| 4,336,804 A | 6/1982 | Roeder |
| 4,337,772 A | 7/1982 | Roeder |

(Continued)

FOREIGN PATENT DOCUMENTS

EP    0418951    7/1995

(Continued)

*Primary Examiner*—George B. Nguyen
*Assistant Examiner*—Ilya Y Treyger
(74) *Attorney, Agent, or Firm*—Kathleen B. Gross

(57) ABSTRACT

The present invention relates to a fastening film system 1 comprising a backing 7 and an adhesive layer 6 on one of the two major surfaces of the backing 7, the backing 7 bearing on its exposed major surface 3a opposite to the adhesive layer 6 a plurality of male fastening elements 4 capable of engaging with fibrous materials 32 having a plurality of complementary female fastening elements, and a plurality of through-holes 2 extending through the thickness 11 of the backing 7 so that the adhesive layer 6 attached to the backing 7 is exposed through such through-holes 2 wherein at least one of said through-holes 2 is encompassed by the backing 7, and wherein the fastening film system 1 releasably adheres to said fibrous materials 32 through a combination of a mechanical and an adhesive bonding mechanism.

19 Claims, 16 Drawing Sheets

U.S. PATENT DOCUMENTS

| | | | |
|---|---|---|---|
| 4,376,440 A | 3/1983 | Whitehead et al. |
| 4,475,913 A | 10/1984 | Hlaban |
| 4,894,060 A | 1/1990 | Nestegard |
| 4,959,265 A | 9/1990 | Wood et al. |
| 5,019,065 A | 5/1991 | Scripps |
| 5,077,870 A | 1/1992 | Melbye et al. |
| 5,300,058 A | 4/1994 | Goulait et al. |
| 5,507,735 A | 4/1996 | Van Iten et al. |
| 5,611,790 A | 3/1997 | Osborn, III et al. |
| 5,676,652 A | 10/1997 | Hunter et al. |
| 5,679,302 A | 10/1997 | Miller et al. |
| 5,759,317 A | 6/1998 | Justmann |
| 5,778,457 A | 7/1998 | Conway |
| 5,858,515 A * | 1/1999 | Stokes et al. ............. 428/195.1 |
| 5,897,545 A * | 4/1999 | Kline et al. ................. 604/386 |
| 6,004,308 A | 12/1999 | Haddock |
| 6,039,717 A | 3/2000 | Larsson |
| 6,051,094 A | 4/2000 | Melbye et al. |
| 6,159,596 A | 12/2000 | Calhoun et al. |
| 6,393,673 B1 | 5/2002 | Kourtidis et al. |
| 6,402,730 B1 | 6/2002 | Malowaniec |
| 6,428,525 B1 | 8/2002 | Malowaniec |
| 6,428,526 B1 | 8/2002 | Heindel et al. |
| 6,443,932 B1 | 9/2002 | Maggiulli |
| 6,524,294 B1 | 2/2003 | Hilston et al. |
| 6,554,816 B1 * | 4/2003 | Olson ........................ 604/386 |
| 6,575,953 B2 | 6/2003 | Olson |
| 6,736,804 B1 * | 5/2004 | Robertson et al. ...... 604/385.13 |
| 2002/0016581 A1 | 2/2002 | Kline et al. |

FOREIGN PATENT DOCUMENTS

| | | |
|---|---|---|
| EP | 0755665 | 1/1997 |
| EP | 0941728 | 9/1999 |
| WO | WO 97/36566 | 10/1997 |
| WO | WO 98/53781 | 12/1998 |
| WO | WO 98/53782 | 12/1998 |
| WO | WO 99/06000 | 2/1999 |
| WO | WO 00/50229 | 8/2000 |
| WO | WO 03/003962 | 1/2003 |

* cited by examiner

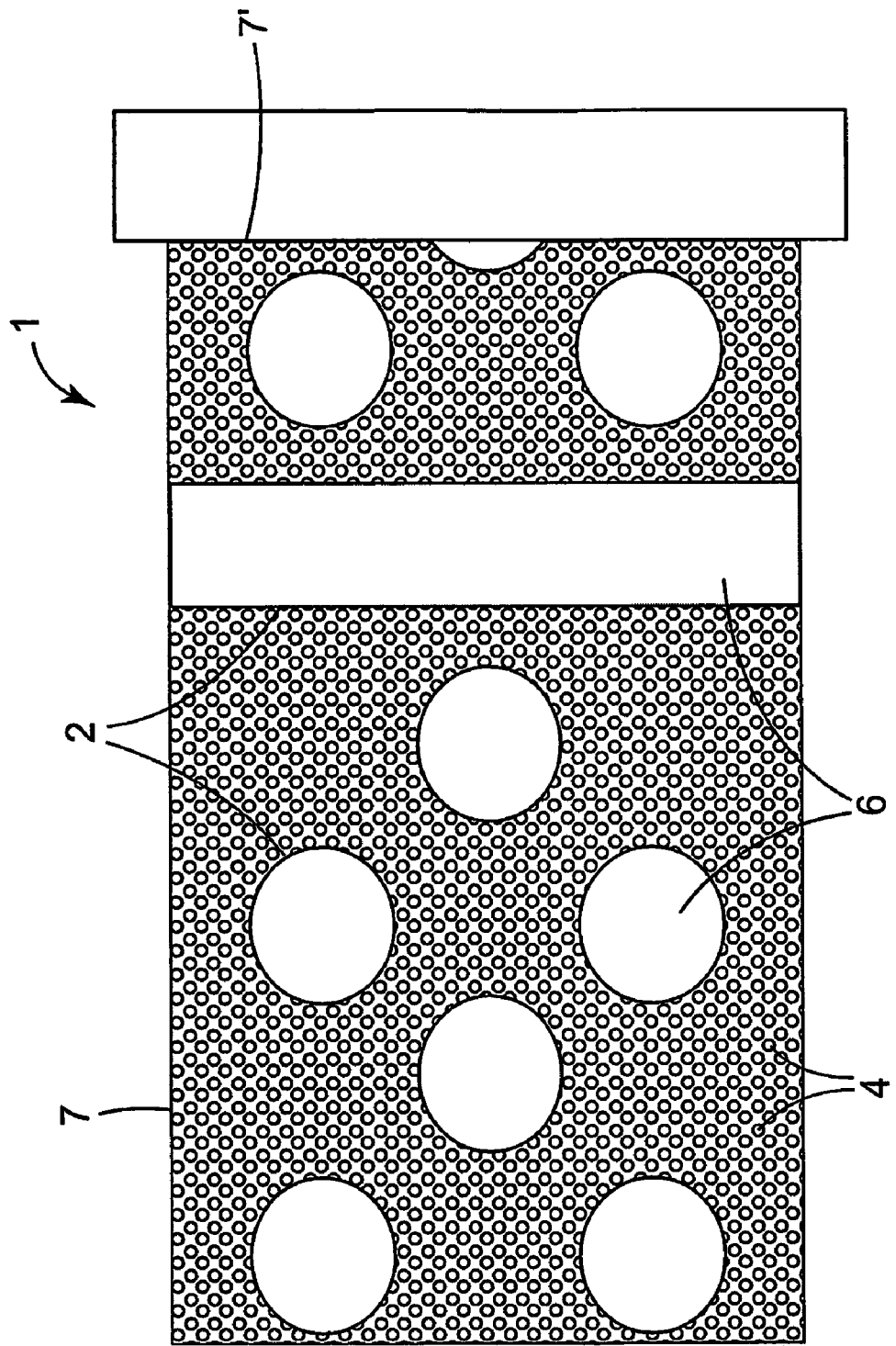

FASTENING FILM SYSTEM AND ASSEMBLY COMPRISING A FASTENING FILM SYSTEM AND A SUBSTRATE

FIELD OF THE INVENTION

The present invention relates to a fastening film system which is suitable for releasably adhering to fibrous materials through a combination of a mechanical and an adhesive bonding mechanism. The present invention furthermore relates to methods of preparing such fastening film systems and to disposable absorbent articles such as diapers or sanitary napkins employing such fastening film systems.

BACKGROUND OF THE INVENTION

EP 0,321,232 discloses a disposable absorbent article such as a diaper comprising a pair of tape tabs attached to an end region of said diaper. Each of the tape tabs exhibits on its respective user's end a fastening surface which has one or two exposed rectangular adhesive areas adjacent to a rectangular strip of a hook fastening element. This construction provides a combination of a mechanical and an adhesive closure mechanism when attaching the tape to the landing member thereby securing the diaper to the wearer's body.

EP 0,974,326 also discloses a disposable absorbent article such as a diaper having a pair of tape tabs attached to a first end region of said diaper and a landing member attached to a second end region of said diaper whereby the user's end of the tape tab comprises both mechanical and adhesive fastening means. It is disclosed that the exposed adhesive area of the tape tab may become contaminated with fiber elements when adhering the tape tab to the fibrous landing member. EP '326 discloses a release treatment of the exposed surface of the fibrous landing member in order to minimize or avoid, respectively, damaging of the fibrous landing member and/or contamination of the exposed adhesive area on the tape tabs.

Fastening film systems providing both a mechanical and an adhesive fastening mechanism are also disclosed in U.S. Pat. Nos. 6,393,673, 6,428,525, 6,402,730, WO 99/06,600 and EP 0,418,951. U.S. Pat. No. '673, for example, describes a mechanical fastening element comprising a multiplicity of flexible hook elements emanating from a backing layer and comprising stems terminating in hook heads wherein the top portions of the hook heads and/or at least part of the interstitial spaces between the stems are coated with a hot-melt pressure-sensitive adhesive.

U.S. Pat. No. 4,959,265 discloses a pressure-sensitive adhesive tape fastener comprising a backing having an array of upstanding stems distributed across at least one face, and a pressure-sensitive adhesive layer filling the spaces between the stems where the average thickness of the adhesive layer is less than the average height of the stems. When adhering the pressure-sensitive adhesive tape fastener to a sanitary napkin, the napkin can be releasably attached to an undergarment by allowing the stems to penetrate into openings of the fabric of the undergarment until the pressure-sensitive adhesive becomes releasably bonded to the fabric.

Attaching the fastening film systems disclosed in U.S. Pat. Nos. 6,393,673, 6,428,525, 6,402,730, WO 99/06,600, EP 0,418,951 and U.S. Pat. No. 4,959,265 to a disposable absorbent article such as a sanitary napkin usually requires providing an additional adhesive layer onto the surface of the fastening film system opposite to the surface bearing the male fastening elements, which may be less advantageous.

Disposable absorbent articles such as sanitary napkins, panty liners and incontinence pads, comprising mechanical and adhesive fastening means arranged separately from each other on different portions of the disposable absorbent article, are known. U.S. Pat. No. 5,676,652 discloses, for example, sanitary napkins comprising adhesive strips on the garment side of the main body of the sanitary napkin and mechanical fasteners on the side wrapping elements. U.S. Pat. No. 5,611,790 discloses sanitary napkins having adhesive fastening means, mechanical fastening means or combinations of adhesive and mechanical fastening means which are arranged separately from each other in patches, for example, on the garment side of the main body of the napkin or on the side wrapping elements.

Sanitary napkins, for example, need to be capable of reliably and releasably adhering to a variety of natural or synthetic fibrous materials such as cotton, silk, nylon, woven, non-woven, knitted and/or microfibrous materials without damaging such materials. These requirements are fulfilled by the sanitary napkins available in the state of the art to an insufficient extent only.

It was therefore an object of the present invention to provide a fastening film system which is capable of releasably adhering to a variety of fibrous materials through a combination of a mechanical and an adhesive bonding mechanism and which does not exhibit the shortcomings of the fastening surfaces of the state of the art or exhibits them to a lower degree only, respectively. Other objects of the present invention will be readily derivable form the following detailed description.

SUMMARY OF THE INVENTION

The present invention relates to a fastening film system comprising a backing and an adhesive layer on one of the two major surfaces of the backing, the backing bearing on its exposed major surface opposite to the adhesive layer a plurality of male fastening elements capable of engaging with fibrous materials having a plurality of complementary female fastening elements, and a plurality of through-holes extending through the thickness of the backing so that the adhesive layer attached to the backing is exposed through such through-holes wherein at least one of said through-holes is essentially completely encompassed by said backing, and wherein the fastening film system releasably adheres to said fibrous materials through a combination of a mechanical and an adhesive bonding mechanism.

The present invention furthermore relates to an assembly comprising a substrate and a fastening film system wherein the adhesive layer of the fastening film system is arranged between the backing of the fastening film system and the substrate.

The present invention furthermore relates to a method of making a fastening film system comprising providing a continuous backing bearing a plurality of male fastening elements, providing a plurality of through-holes extending through the thickness of the backing wherein at least part of said through-holes is essentially completely encompassed by said backing, and laminating the resulting backing onto an adhesive layer.

The present invention furthermore relates to another method of making a fastening film system of the present invention comprising providing a continuous backing bearing a plurality of male fastening elements, providing one or 2n+1 continuous cuts with n being an integer in the machine direction, into the backing so that the cut which has a periodic sequence of notches and protrusions characterized by a wavelength and an amplitude, forms the 2 or 2n adjacent sub-backings, separating the 2 or 2n adjacent sub-backings by about at least the amplitude in the cross-direction and by about half of the wavelength or a multiple of such half of the wavelength, respectively, in the machine direction, and moving the 2 or 2n sub-backings towards each thereby creating a sequence of through-holes between the two sub-backings which are at least partly encompassed by the backing, and attaching an adhesive layer to the surface of the sub-backings opposite to the surface bearing a plurality of male fastening elements.

The present invention furthermore relates to a method of making an assembly of the present invention comprising providing a substrate and applying an adhesive layer to an exposed surface of such substrate, providing a continuous backing bearing on one of its major surfaces a plurality of male fastening elements, further providing a plurality of through-holes extending through the thickness of the backing, and attaching the resulting backing comprising through-holes through its major surface which is opposite to the major surface bearing a plurality of male fastening elements, to the exposed surface of the adhesive layer.

The present invention furthermore relates to another method of making an assembly of the present invention comprising providing a substrate and applying an adhesive layer to an exposed surface of such substrate, providing a continuous backing bearing on one of its major surfaces a plurality of male fastening elements, providing one or 2n+1 continuous cuts with n being an integer, in the machine direction into the backing so that the cut which has a periodic sequence of notches and protrusions characterized by a wavelength and an amplitude, forms 2 or 2n adjacent sub-backings, separating adjacent sub-backings by about at least the amplitude in cross-direction and by about half of the wavelength or a multiple of such half of the wavelength, respectively, in the machine direction, and moving the 2 or 2n sub-backings towards each other thereby creating a sequence of through-holes between the two sub-backings, and attaching the resulting construction of sub-backings through the major surfaces of such sub-backings which are opposite to the major surfaces bearing a multitude of male fastening elements, to the exposed surface of the adhesive layer.

The present invention furthermore relates to a disposable absorbent article such as a diaper or a sanitary napkin comprising a liquid-permeable top sheet, a liquid-impermeable back sheet opposite to said top sheet, a liquid-absorbent core between said top sheet and said back sheet, longitudinal edges, a first end region and a second end region, the absorbent article further comprising the fastening film system or assembly according to the present invention in order to secure said disposable absorbent article to the body and/or to the undergarment or panties of a person.

BRIEF DESCRIPTION OF THE FIGURES

FIG. 1b is a cross-section along the line 1b-1b of the preferred embodiment of the fastening film system 1 of FIG. 1a.

FIG. 1d is a top view of a preferred embodiment of a fastening film system of the invention.

FIG. 2b is a cross-section along the line 2b-2b of the preferred embodiment of the assembly of FIG. 2a.

FIG. 6b is a cross-section along the line 6b-6b of the tape tab 27 of the diaper 20b of FIG. 6a.

FIG. 7a is a schematic exploded view of a specific embodiment of a sanitary napkin 20a.

FIG. 7b is a top view of a specific embodiment of a sanitary napkin 20a.

FIG. 7c is a top view of another specific embodiment of a sanitary napkin 20a.

DETAILED DESCRIPTION OF THE INVENTION

Figure 1A:
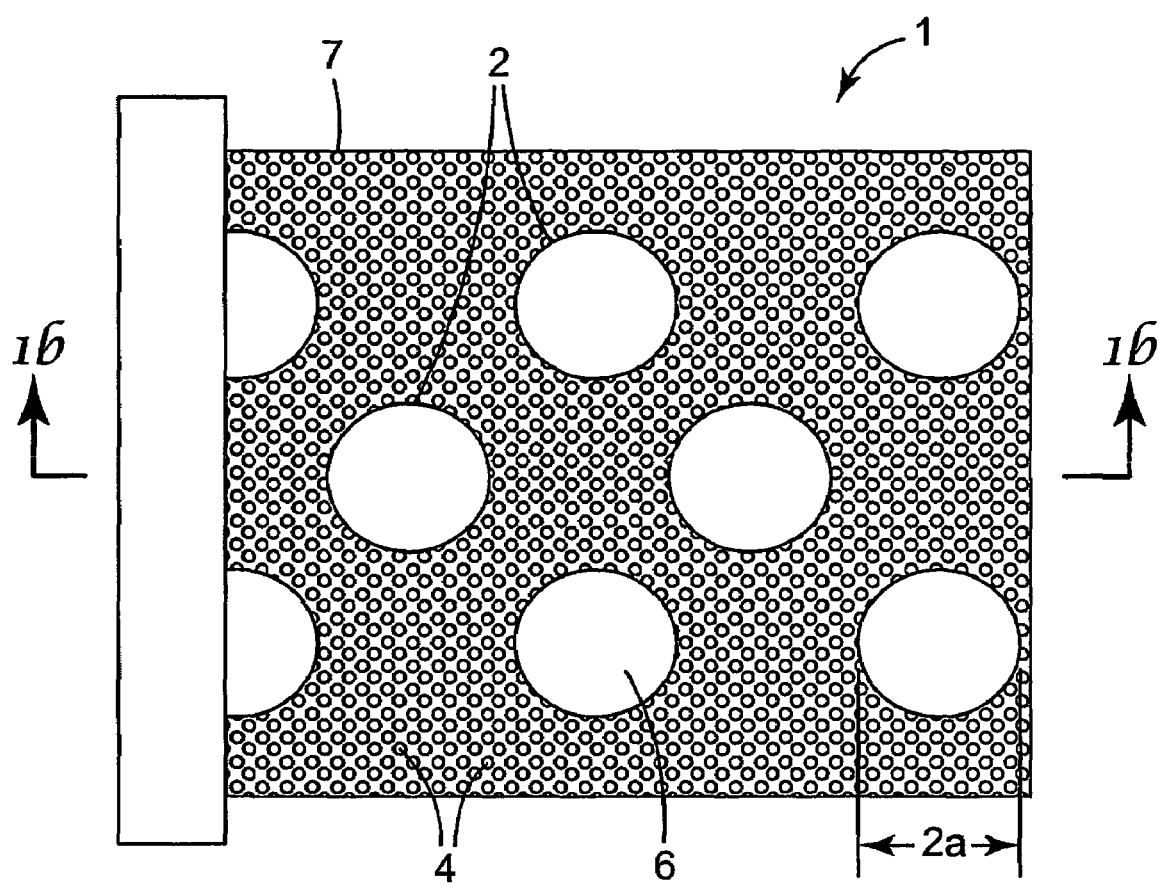
FIG. 1a is a top view of a preferred embodiment of a fastening film system 1 of the invention.

The present invention relates to a fastening film system 1 comprising a backing 7 having two major surfaces 3a and 3b. The term "film" as used above and below indicates that the fastening film system 1 has extensions in two directions termed as the machine direction (MD) and the cross-direction (CD) which independently from each other distinctly exceed the extension of such fastening film system 1 in a third direction normal to MD and CD, respectively. The term "system" as used above and below is intended to indicate that the fastening film system 1 comprises at least a backing 7 and an adhesive layer 6.

The term "machine direction" (MD) as used above and below denotes the direction of the running, continuous web of the backing 7 during the manufacturing of the fastening film system 1. In the embodiment of the continuous web of backing 7 shown in FIG. 3a, the machine direction corresponds to the direction of the longitudinal edges of the web of the backing 7. The term "cross-direction" (CD) as used above and below denotes the direction which is essentially normal to the machine direction.

The exposed major surface 3a of the backing 7 of the fastening film system 1 of the present invention bears a plurality of male fastening elements 4 capable of engaging with fibrous materials 32 having a plurality of complementary female fastening elements. An adhesive layer 6 is attached to the major surface 3b of the backing 7 of the fastening film system 1 opposite to its exposed major surface 3a. The backing 7 furthermore comprises a plurality of through-holes 2 exposing the adhesive of adhesive layer 6 thereby providing an adhesive bonding mechanism to said fibrous materials 32 in addition to the mechanical bonding mechanism effected by the male fastening elements 4.

The backing 7 preferably is an essentially flat continuous film that may be formed by cast molding or extrusion molding. Substantially any thermoplastic material suitable for film production can be used to produce the backing. Preferred thermoplastic resins include polyesters such as poly(ethylene terepthalate), polyamides such as nylon, poly(styrene-acrylonitrile), poly(acrylonitrile-butadiene-styrene), polyolefins such as polypropylene, and plasticized polyvinylchloride.

The exposed major surface 3a of the backing 7 preferably is essentially flat but it may also exhibit a pattern and the thickness 11 of the backing 7 may, for example, be higher in areas adjacent to the through-holes 2 as compared to areas between the through-holes 2.

The backing 7 may comprise only one material and exhibit an essentially uniform construction in CD, but it may also comprise a sequence of two or more zones in CD having different properties whereby such zones preferably extend continuously in MD.

The thickness 11 of backing 7 which is essentially flat or the effective thickness of a backing which is not essentially flat, in the areas adjacent to the through-holes 2, respectively, preferably is between 10 µm and 1 mm, more preferably between 12 µm and 800 µm and especially preferably between 15 µm and 750 µm. If the thickness is above 1 mm, the interaction between the adhesive area exposed through the through-holes 2 and a fibrous material 32 being brought into contact with the fastening film system 1 tends to be too weak so that no or an insufficient adhesive bonding mechanism is present between the fastening film system 1 and such fibrous material 32. If the thickness 11 of the backing 7 is less than 10 µm, the adhesive bonding mechanism tends to dominate the interaction between the fastening film system 1 and such fibrous material 32 to such an extent that especially lofty fibrous materials 32 may be damaged upon separating and rebonding the fastening film system 1 to the substrate. If the thickness of the backing 7 is less than 10 µm, the mechanical stability of the backing 7 bearing male fastening elements 4 also tends to be too low.

The exposed major surface 3a of the backing 7 exhibits a plurality of male fastening elements 4. The male fastening elements preferably have a hook shape, and they usually comprise a stem 4a supported by the exposed major surface 3a of the backing 7 and an enlarged section 4b which is positioned at the end of the stem opposite to the exposed major surface 3a of the backing 7. The male fastening elements 4 can also be formed by stems 4a having no enlarged section at the end of the stem 4a opposite to the backing whereby such stems 4a preferably are essentially conical, cylindrical or pyramidal.

The male fastening elements 4 preferably are integral with the exposed major surface 3a of the backing 7 but it is also possible that the male fastening elements 4 are bonded individually or in form of patches each having a support layer bearing one or more male fastening elements 4 to the exposed major surface 3a of the backing 7. Bonding of such individual fastening elements 4 or patches of fastening elements 4, respectively, can be effected, for example, by adhesive bonding, by ultrasonic bonding, by thermal bonding or by stitching. It is disclosed, for example, in WO 00/50,229 to apply discrete hook patches to the exposed surface 3a of a backing 7.

The enlarged section 4b of the male fastening elements 4 may have any shape such as hooks, T's, J's, mushroom-type heads (including concavely curved heads and disc-shaped heads) or any other shape allowing for engagement with complementary female fastening elements.

Male fastening elements 4 suitable in the present invention can be manufactured from a wide range of materials including thermoplastic polymers such as, for example, nylon, polyester, polyolefins or any combination of these. The male fastening elements 4 preferably comprise the material of which the backing 7 is formed.

The dimensions of the individual male fastening elements 4 can be varied widely depending on the application and the structure and loftiness of the complementary female fibrous material 32. When employing the fastening film system 1 of the present invention, for example, in disposable sanitary articles such as incontinence articles, diapers or napkins, the male fastening elements 4 comprising stems 4a and, optionally, an enlarged section 4b at the end of the stem opposite to major surface 3a, preferably are between 40 µm and 2 mm in height above the backing. The stems 4a preferably have a cross-section with a maximum extension of between 10 µm and 250 µm. The ratio of the maximum extension of the enlarged portions 4b of the male fastening elements 4 at the end of the stems 4a opposite to the exposed major surface 3a of the backing 7, over the maximum extension of the cross-sections of the stems 4a preferably is between 1.5:1 and 5:1.

The average surface density of the male fastening elements 4 with respect to the total surface area of the backing 7 (including the surface area of through-holes 2) may vary broadly and preferably is between $10/cm^2$ and $5,000/cm^2$, more preferably between $20/cm^2$ and $4,000/cm^2$ and especially preferably between $25/cm^2$ and $3,500/cm^2$. If the density of the male fastening elements 4 is less than $10/cm^2$ the strength of the mechanical bonding mechanism between the fastening film system 1 and a fibrous material 32 brought into contact with the fastening film system 1, tends to be insufficient for practical purposes. If the density of the male fastening elements 4 is above $5,000/cm^2$, the single fastening elements 4 tend to be very small and may not mechanically engage with the fibrous material 32 sufficiently.

A preferred mushroom-type hook web including a homogenous backing 7 of thermoplastic resin and, integral with the backing 7, an array of upstanding stems 4a projecting from the surface 3a of the backing 7 and having a mushroom head 4b at the end of the stem 4a opposite to the surface of the backing 7, is disclosed, for example, in U.S. Pat. No. 5,077, 870. This mushroom-type hook strip can be obtained by feeding the molten thermoplastic resin through a die to a rotating cylindrical mold which has cavities that are negatives of the upstanding stems 4a. The molten resin is injected into the cavities in an excess of an amount that would fill the cavities so that a backing 7 is formed. The resin is solidified and then stripped from the mold as a web that has an array of upstanding stems 4a. The web is then passed between two calendar rolls whereby the roll contacting the tip of the stems 4a is heated to allow for formation of the mushroom heads 4b. U.S. Pat. No. 5,679,302 discloses another mushroom-type hook strip where the enlarged portion 4b at the end of the stems is essentially disc-shaped.

Male fastener webs comprising a homogenous backing 7 and, integral with the backing 7, an array of male fastening elements 4 whereby the enlarged portions 4b have a variety of shapes, is disclosed, for example, in U.S. Pat. No. 4,894,060.

The male fastener webs and the specific geometry of the individual fastening elements 4 disclosed in U.S. Pat. Nos. 5,077,870, 5,679,302 and U.S. Pat. No. 4,894,060 are described here only by way of example and are not intended to limit the invention in any way. Other non-limiting examples of suitable male fastener webs are described, for example, in U.S. Pat. No. 4,984,339 and U.S. Pat. No. 5,781, 969.

The backings 7 exhibit a plurality of through-holes 2 which can be obtained, for example, by die-cutting, punching, cutting or stretching, or they may be formed directly when manufacturing the fastener web. The through-holes 2 extend throughout the thickness 11 of the backing 7, i.e., they connect two openings one opening being in the exposed major surface 3a of the backing 7 bearing a plurality of male fastening elements 4 and the other opening being in the major surface 3b of the backing 7 opposite to its exposed major surface 3a. The two openings are arranged so that they partly overlap in a direction normal to MD and CD, i.e., an observer viewing at the backing in a direction normal to MD and CD can look through the through-holes 2. The through-holes 2 can also be formed by two adjacent parts of a backing 7, 7' as is shown in FIG. 1d.

Figure 1B:
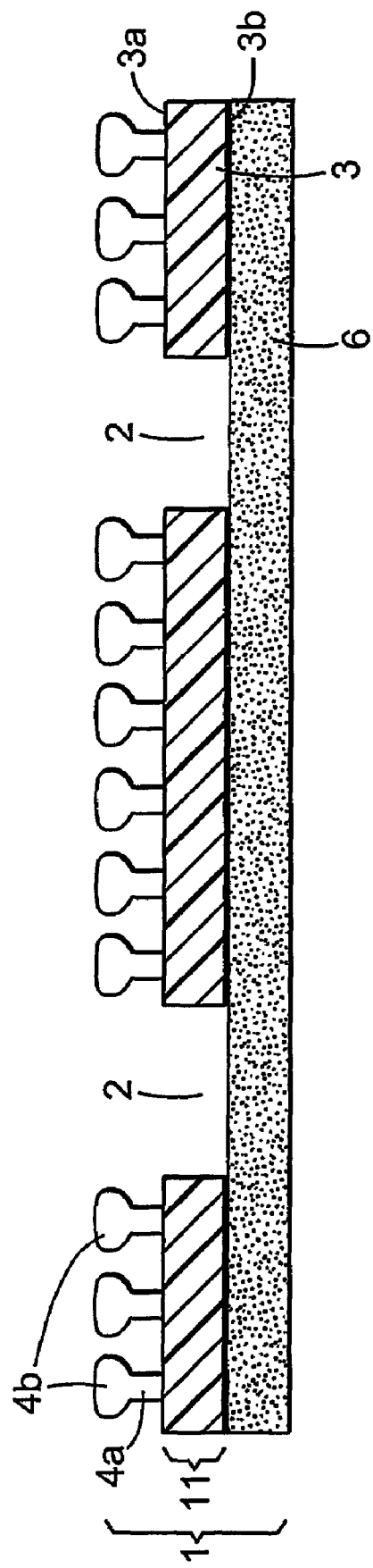

The through-holes 2 preferably extend essential normal to the MD and the CD as is shown, for example, in FIG. 1b but it is also possible that the through-holes 2 extend in a direction oblique to the direction which is normal to MD and CD. The effective cross-section of a through-hole 2 is the area seen by an observer when viewing at the backing in a direction normal to MD and CD. The sum of such areas is referred to above and below as the surface area of the through-holes 2.

The ratio of the surface area of the through-holes 2 relative to the surface area of the backing 7 (prior to cutting, i.e. the surface area of the backing 7 including the surface area of the through-holes 2) preferably is between 15 and 85%, more preferably between 20 and 75% and especially preferably between 35 and 65%.

The average value of the maximum effective extension of the through-holes 2 preferably is between 1 and 50 mm, more preferably between 1 and 40 mm and especially preferably between 1 and 35 mm. The term maximum effective extension refers to the maximum possible distance between two points of the effective cross-section of through-holes 2 as seen by an observer viewing in a direction normal to CD and MD.

If the average value of the maximum effective extension of the through-holes 2 is less than 1 mm, the exposed adhesive of such through-holes 2 tends not to form a sufficient adhesive bonding mechanism between the fastening film system 1 and a fibrous material 32 brought into contact with the fastening film system 1. If the average value of the maximum effective extension of the through-holes 2 is more than 50 mm, the adhesive bond between the fastening film system 1 and fibrous materials 32 tends to be too strong which may result in damaging said fabric, in particular, lofty, fibrous materials 32.

The average surface density of through-holes 2, i.e. the average number of said through-holes 2 per surface unit, preferably is between $100/m^2$ and $40,000/m^2$, more preferably between $250/m^2$ and $20,000/m^2$ and especially preferably between $250/m^2$ and $17,500/m^2$.

The average distance between adjacent through-holes 2 preferably is at least 1 mm, more preferably at least 1.2 mm and especially preferably at least 1.5 mm. If the average distance between two adjacent through-holes is less than 1 mm, the adhesive bonding mechanism between the adhesive exposed through such through-holes 2 and a fibrous material 32 brought into contact with the fastening film system 1 tends to be too high for many applications. Furthermore, if the average distance between two adjacent through-holes 2 is less than 1 mm, the surface density of the male fastening elements 4 tends to be too low. The average distance between adjacent through-holes 2 preferably is less than 15 mm, more preferably less than 10 mm and especially preferably less than 8 mm.

The effective cross-section of the through-holes 2 may exhibit various shapes such as, for example, circular, rectangular, triangular, ellipsoid, essentially trapezoid or more complicated regular or irregular shapes.

The through-holes 2 may be completely or partly encompassed by the backing 7. Through-holes 2 which are only partly encompassed by the backing 7 may be present, for example, at the edges of a piece of a fastening film system 1 as is illustrated, for example, in FIG. 1a. It is also possible, for example, that the fastening film system 1 comprises an exposed adhesive strip continuously extending in MD as is illustrated in FIG. 1d. In FIG. 1d, the exposed adhesive strip and the through-holes arranged at the edges of the two parts of a backing 7, 7' form through-holes 2 which are not fully encompassed by the backing 7, 7' whereas the other through-holes of the fastening film system 1 of FIG. 1d are fully encompassed by the backing 7, 7'.

It is exemplified in FIG. 3a-3d that two sub-webs 7a, 7b each having a plurality of partly encompassed through-holes 2 defined by cuts 8, may be rearranged into an adjacent placement to form a plurality of essentially completely encompassed through-holes 2.

It is essential in the present invention that at least one of the through-holes 2, preferably at least $50/m^2$, more preferably at least $100/m^2$ and especially preferably at least $150/m^2$, are completely encompassed by the backing 7. The ratio of the number of through-holes 2 which are completely encompassed by the backing 7 over the total number of through-holes 2 preferably is at least 0.5, more preferably at least 0.75 and especially preferably at least 0.8.

It was found by the present inventors that a well balanced combination of an adhesive and a mechanical bonding mechanism with respect to a variety of fibrous materials 32 can only be obtained if at least one of the through-holes 2 is fully encompassed by the backing 7. If no fully encompassed through-holes 2 are present, the adhesive bonding mechanism of the fastening film system 1 or the assembly 40, respectively, towards various fibrous materials 32 as evaluated, for example, by the measurement of the 90° peel adhesion values referred to below, may differ distinctly so that fibrous materials 32 experiencing a strong adhesive interaction with the respective fastening film system 1 or the assembly 40, respectively, may be damaged as a result of such strong adhesive interaction. It was also found that fastening film systems of the present invention comprising at least one fully encompassed through-hole 2, tend to exhibit a lower value of the adhesive bonding mechanism in comparison to a fastening film system comprising the same surface area of the through-holes relative to the surface area of the backing 7 prior to cutting but no fully encompassed through-holes 2. Because of such better control of the adhesive bonding mechanism, damaging of the fibrous material 32 is less likely.

It was furthermore found by the present inventors that a well-balanced combination of an adhesive and a mechanical bonding mechanism with respect to a variety of fibrous materials 32 can be obtained if the sum of the maximum densities of the through-holes 2 along the extension of the backing 7 and/or the adhesive layer 6 in the CD and in the MD preferably is at least 1 $cm^{-1}$, more preferably at least 1.3 $cm^{-1}$ and especially preferably at least 1.5 $cm^{-1}$. Such embodiments of the fastening film system 1 and the assembly 40 are especially preferred.

Figure 1C:
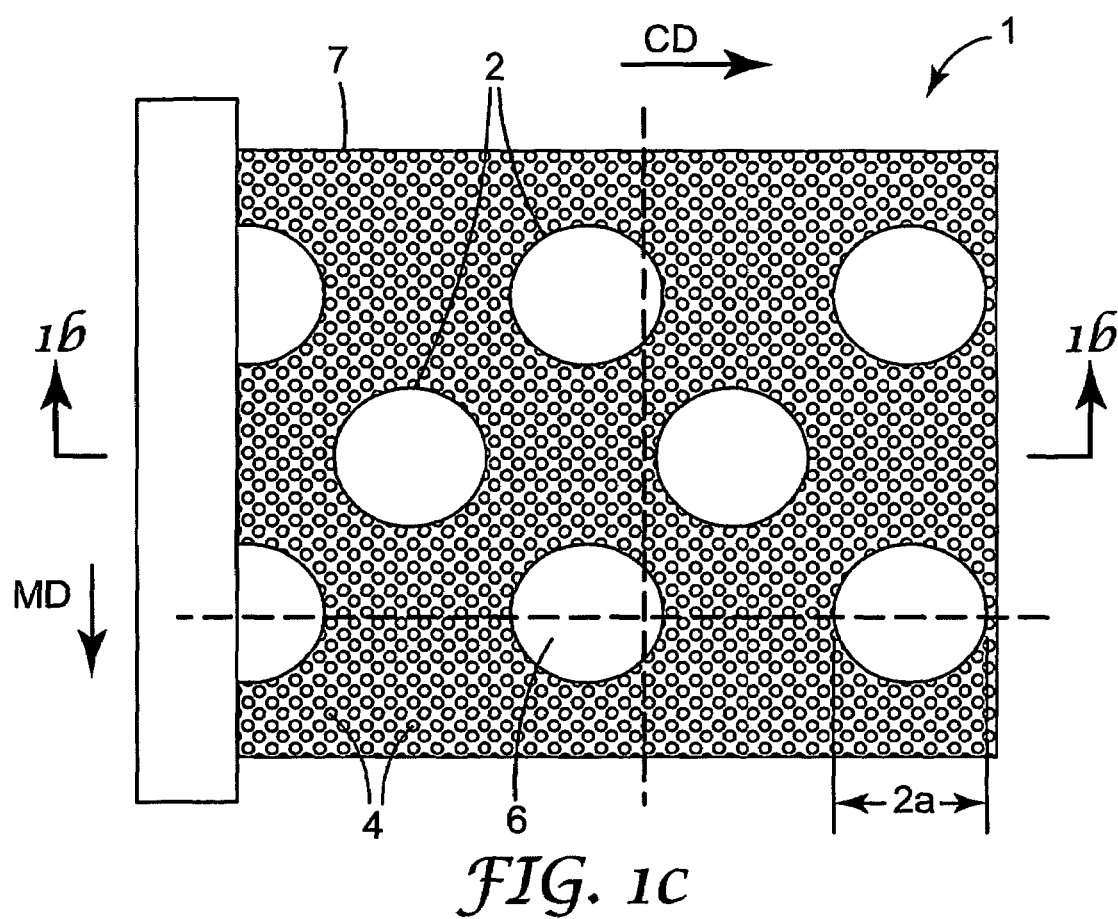
FIG. 1c is a top view of the fastening film system 1 of FIG. 1a additionally comprising dotted lines in the MD and in the CD used to evaluate the maximum densities of the through-holes 2 in such directions.

In order to determine such maximum density in the CD and in the MD, the maximum number of through-holes 2 in such directions is determined as is schematically indicated in FIG. 1c for the portion of the fastening film of FIG. 1a.

When applying a dotted auxiliary line, for example, in the CD and shifting it parallel to the CD along the extension of the fastening film system 1, it is easily established that the maximum number of through-holes 2 in the CD is 3; this can be seen, for example, when counting the number of through-holes 2 in the CD along the dotted line included in FIG. 1c. Likewise, when applying a dotted auxiliary line in the MD so that it intersects or touches, respectively, as many through-holes as possible, it is easily established that the maximum number of through-holes 2 in the MD is 3 (see FIG. 1c). The dotted lines are imaginary auxiliary lines only and they are included in FIG. 1c for determining the maximum number of through-holes in the CD and in the MD, respectively.

The maximum densities in the CD and in the MD are obtained by dividing these numbers by the respective extension of the adhesive layer 6 in the CD and in the MD, respectively. These densities are then summed up.

The major surface 3b of the backing 7 opposite to its exposed major surface 3a, bears an adhesive layer 6 which may be continuous or discontinuous. The adhesive layer 6 extends on the major surface 3b of the backing 7 (at least partly) in the area of the through-holes 2 so that the adhesive which is present in the area of the through-holes 2 is exposed. The average ratio of the exposed area of the adhesive layer 6 over the surface area of the through-holes 2 preferably is at least 0.75, more preferably at least 0.9 and especially preferably essentially 1.0.

The adhesive of adhesive layer 6 is preferably selected from a group of adhesives having a 90° peel adhesion to a smooth polyethylene test surface as measured according to ASTM D3330F using a roll-down weight of 5,000 g, of between 1 N/inch and 10 N/inch, more preferably of between 1.5 N/inch and 8 N/inch and especially preferably of between 2 N/inch and 8 N/inch. If the 90° peel adhesion is less than 1 N/inch, the adhesive bonding mechanism between the fastening film system 1 and a fibrous material 32 brought into contact with it, tends to be undesirably low in many cases. Also, for such low values of 90° peel adhesion, it tends to be difficult to optimize the performance of the fastening film system 1 with respect to a variety of fibrous materials 32 including both lofty-type fabrics such as cotton based fabrics or more densely woven fabrics such as, for example, nylon based fabrics. If the 90° peel adhesion is higher than 10 N/inch, the adhesive bonding mechanism between the fastening film system 1 and a fibrous material 32 brought into contact with it, tends to be undesirably strong in many cases so that the fibrous material 32 may be damaged. Tacky adhesives which are useful in the present invention preferably include pressure-sensitive adhesives which are selected from a group comprising (meth)acrylate and/or natural or synthetic rubber-based pressure-sensitive adhesives. Rubber-resin additives preferably comprise in addition to the rubber materials one or more tackifying resin in order to render the rubber materials tacky. Preferred examples of rubber-based pressure-sensitive adhesives are the polystyrene-polyisoprene block copolymers tackified with synthetic polyterpene resins. Suitable acrylate-based pressure-sensitive adhesives are disclosed, for example, in U.S. Re 24,906 or U.S. Pat. No. 4,710,536. Suitable synthetic rubber based adhesives are described, for example, in U.S. Pat. No. 5,019,071 and U.S. Pat. No. 3,932,328.

The adhesive layer 6 may be applied to the major surface 3b of the backing 7 opposite to its exposed major surface by lamination. When preparing an assembly 40 according to the present invention, the adhesive layer 6 is preferably first applied to an exposed surface of a substrate 5 by coating or lamination, and the backing 7 is then applied to the adhesive layer 6 through its major surface 3b.

The dimensions of the adhesive layer 6 in CD and/or MD may essentially match with the corresponding dimensions of the backing 7 but it is also possible that the dimensions of the adhesive layer 6 in CD and/or MD differ and, in particular, exceed the dimensions of the backing 7. The assembly 40 shown in FIGS. 2a and 2b and in FIG. 6b, for example, comprises adhesive layer 6 the dimensions of which exceed the dimensions of the corresponding backing 7.

The through-holes 2 are preferably introduced into the backing 7 prior to applying the adhesive layer 6 but it may also be possible to introduce the through-holes subsequently to the application of the adhesive layer 6 by kiss-cutting.

The backing 7 may be subjected to monoaxial or biaxial stretching prior to or subsequent to the application of the adhesive layer 6, respectively. Monoaxial stretching can thus be applied to the backing 7, to the fastening film system 1 or to the assembly 40, respectively, in MD or CD, and biaxial stretching can be applied to the backing 7, to the fastening film system 1 or to the assembly 40, respectively, subsequently or simultaneously in CD and MD. The term stretch ratio as used above and below denotes the ratio of a linear dimension of a given portion of the stretched backing 7, the fastening film system 1 or the assembly 40, respectively, to the linear dimension of the same portion of the backing 7, the fastening film system 1 or the assembly 40, respectively, prior to stretching. The stretch ratios in MD and CD preferably are independently from each other between 1.1:1 and 8:1 and more preferably between 1.1:1 and 5:1. Biaxial stretching is preferred. Monoaxial stretching or sequential biaxial stretching can be performed, for example, by propelling a continuous web of the backing 7, the fastening film system 1 or the assembly 40, respectively, in the respective direction over rollers of increasing speed. Simultaneous biaxial stretching can be performed, for example, by using a flat film tenter apparatus as is described, for example, in U.S. Pat. Nos. 4,675,582, 4,825,111, 4,853,602, 5,036,262, 5,051,225 and U.S. Pat. No. 5,072,493.

Stretching which can be applied to a backing 7 prior to introducing the through-holes 2 or to a backing 7 comprising through-holes, to the fastening film system 1 or to the assembly 40, respectively, effects various parameters of the backing 7, the fastening film system 1 or the assembly 40 such as, for example, the thickness of the backing 7, of the adhesive layer 6 and of the substrate 5, the shape and/or the density of the male fastening elements 4, and the shape and the average value of the maximum effective extension of the through-holes 2. The person skilled in the art can select the stretch ratio and the mode of stretching, i.e., monoaxial or biaxial stretching, to vary and optimize such parameters within the preferred ranges as specified above.

In another preferred embodiment of the present invention, the backing 7 comprising through-holes 2 may be an extrusion-formed reticulated web, mesh or netting comprising two sets of strands at angles to each other. A preferred method of making such nettings includes extruding a thermoplastic resin through a die plate which is shaped to form a base film layer having a first set of spaced supporting ridges or ribs projecting from one major surface of the base layer film and a second set of ridges or nibs exhibiting a cross-sectional profile of a male fastening element 4 such as a hook projecting from the other major surface of the base film layer. The spaced supporting ridges or ribs formed on one major surface of the base film layer form the first set of strands forming the reticulated mesh or netting. The second set of transverse strands are formed by transversely cutting the opposite major surface of the base film layer comprising the second set of ridges or ribs, to form discrete cut members. Subsequently longitudinal stretching of the backing layer in the direction of the first set of the supporting ridges or ribs, i.e., in MD, separates these discrete cut portions. The cut portions then form the second set of spaced-apart strands bearing male fastening elements 4 such as hooks that have a cross-sectional shape identical to the cross-sectional shape of the second set of nibs or ridges.

The two sets of spaced-apart strands obtained in such method form the backing 7 bearing male fastening elements 4, and the openings in the mesh or netting structure form the through-holes 2. The dimensions of the supporting ridges or ribs and the spacing between adjacent supporting ridges or ribs is preferably selected to provide sufficiently large through-holes 2. The dimension of the through-holes 2 is influenced by the spacing between adjacent ridges or ribs of the first set of supporting ridges or ribs, by the spacing between the cut-lines through the second set of ridges or nibs having, for example, a hook-shaped cross-section and by the stretching ratio of longitudinal stretching in MD.

The person skilled in the art can select and modify these parameters to vary and optimise the dimension of the through-holes 2 and the adjacent areas of the backing 7, respectively.

Mesh or netting structures and methods of preparing them are disclosed, for example, in the co-pending patent application U.S. Ser. No. 10/376,979 filed by the present applicant on 28 Feb. 2003 with the U.S. Patent and Trademark Office. It is also possible on all or preferably on part of the exposed major surface 3a of the backing 7, that the enlarged sections 4b of the male fastening elements and/or the interstitial spaces between the stems 4a of the male fastening elements 4 comprise a pressure-sensitive adhesive. In this case, the adhesive bonding mechanism is provided through the adhesive on and/or between the male fastening elements on the exposed major surface 3a of the backing 7 and through the adhesive layer 6 exposed through the through-holes 2. This construction allows to further modify and tailor-make the ratio of the adhesive bonding mechanism relative to the mechanical bonding mechanism.

In a preferred embodiment of the present invention the fastening film system 1 of the present invention forms part of an assembly 40 which additionally comprises a substrate 5. The fastening film system 1 is preferably attached through its adhesive layer 6 to an exposed surface of the substrate 5.

The substrate 5 may be formed by a variety of materials and constructions. In one preferred embodiment the substrate 5 is a disposable absorbent article such as a sanitary napkin 20a. The fastening film system 1 is preferably attached, through its adhesive layer 6, to the back sheet 22 of such sanitary napkin 20a which is facing the wearer's garment during use.

In another preferred embodiment the substrate 5 is formed by the support film 34 of a tape tab 27 which may be used in a disposable absorbent article such as a diaper 20b. As is illustrated, for example, in FIG. 6a, the tape tab 27 may form part of the closure system of a diaper 20b comprising a pair of such tape tabs 27 and the landing zone 28 comprising a fibrous material 32. In the specific construction shown in FIG. 6b the support layer bears a continuous adhesive layer 6 which is used in the manufacturer's end 27a of the support film 34 to secure the tape tab 27, for example, to the back sheet 22 of the diaper 20b. In the user's end 27b of the support film, the backing 7 comprising through-holes 2 and bearing male fastening elements 4 on its exposed major surface 3a, is attached through its opposite major surface 3b to the adhesive layer 6 thereby forming an assembly 40.

The support film 34 may comprise only one material and exhibit an essentially uniform construction in CD but it may also comprise a sequence of two or more zones in CD having different properties whereby such zones preferably extend continuously in MD.

The term "zone" as used above and below refers to a section of the support film 34 in CD exhibiting an essentially uniform construction and/or uniform properties. The different zones can be formed by different materials which are joined to each other, for example, by adhesive means such as pressure-sensitive adhesive means, ultrasonic bonding, thermal bonding, mechanical bonding, stitching or any combination of these bonding methods. It is, however, also possible that different zones are created by "activating" one or more zones of the web. As used above and below, the term "activating" means subjecting the support film 34, for example, to a mechanical, thermal, electrical and/or chemical treatment in order to impart different functionalities to the treated zones of the web.

The different zones of the support film 34 may consist essentially of one material but it is also possible that the zones comprise a sequence of two or more layers of materials and/or exhibit substructures in the direction essential normal to MD and CD.

One or more zones of the support film 34 preferably comprise a carrier film in order to impart structural integrity and/or stiffness to the support film in CD. The carrier film may be selected from a variety of films or sheetings including single- or multilayered films, coextruded films, laterally laminated films or films comprising foam layers. The layers of such films or sheetings may comprise various materials such as, for example, polypropylene, polyvinylchloride, polyethylene terephthalate, polyethylene, polyolefin copolymers or blends of polyolefins such as, for example, a blend of polypropylene, LPDE (low density polyethylene) and/or LLDPE (linear low density polyethylene), textiles, and non-woven and foamed materials. The thickness of the carrier film is preferably between 30 and 500 µm and more preferably between 40 and 150 µm. The base weight of the backing is preferably between 15 and 500 g/m$^2$, more preferably between 20 and 300 g/m$^2$ and especially preferably between 20 and 200 g/m$^2$.

The different zones of the support film 34 may consist essentially of one material but it is also possible that the zones comprise a sequence of two or more layers of materials and/or exhibit substructures in the direction essential normal to MD and CD.

One or more zones of the support film 34 preferably comprise a carrier film in order to impart structural integrity and/or stiffness to the support film in CD. The carrier film may be selected from a variety of films or sheetings including single- or multilayered films, coextruded films, laterally laminated films or films comprising foam layers. The layers of such films or sheetings may comprise various materials such, as for example, polypropylene, polyvinylchloride, polyethylene terephthalate, polyethylene, polyolefin copolymers or blends of polyolefins such as, for example, a blend of polypropylene, LPDE (low density polyethylene) and/or LLDPE (linear low density polyethylene), textiles, and non-woven and foamed materials. The thickness of the carrier film is preferably between 30 and 500 µm and more preferably between 40 and 150 µm. The base weight of the backing is preferably between 15 and 500 g/m$^2$, more preferably between 20 and 300 g/m$^2$ and especially preferably between 20 and 200 g/m$^2$.

One or more zones of the support film 34 may comprise one or more elastically extensible materials extending in at least one direction when a force is applied and returning to approximately their original dimension after the force is removed.

Elastically extensible materials which are useful in the present invention include materials which preferably are elastically extensible without requiring an activation step. Such materials include elastic, natural or synthetic rubber, rubber foams, elastomeric scrims, woven or non-woven elastomeric webs, elastomeric composites, zero-strain stretch laminates or prestrained stretch laminates.

The elastically extensible materials may be made from a group of materials comprising essentially isotropic or essentially anisotropic materials, respectively. Useful elastic materials preferably exhibit an elongation at break as measured according to ASTM D 882 in the preferred direction of stretchability of at least 25% or more and, more preferably, of more than 50% and most preferably of more than 100%.

Preferred essentially isotropically elastic materials include elastomeric polyurethane materials, or natural or synthetic rubber materials such as, for example, ethylene-propylene-dien copolymers (EPDM), styrene-butadiene-styrene block copolymers (SBS) or styrene-(ethylene-butylene)-styrene block copolymers (SEBS). Elastomeric materials of the A-B or A-B-A block copolymer type which are useful in the present invention, include, for example, those described in U.S. Pat. Nos. 3,265,765, 3,562,356, 3,700,633, 4,116,917 and U.S. Pat. No. 4,156,673. Other elastomeric materials which may be used to form the elastic means include elastomeric polyamide materials and elastomeric polyolefin and polyester materials. Blends of these elastomers with each other or with modifying non-elastomers are also contemplated. For example, up to 50 wt. %, but preferably less than 30 wt. % with respect to the mass of the elastomeric material can be added as stiffening aids such as polyvinylstyrenes, polystyrenes, polyesters, epoxies, polyolefins or coumarone-indene resin. These stiffening aids tend to improve the flexibility of the elastomeric materials.

Preferred elastic materials are commercially available from Exxon Mobil Corp. under the trademark Vector and from Kraton Polymers Comp. under the trademark Kraton.

Additionally or alternatively it is also possible to subject one or more zones of the support film 34 to an activation treatment in order to render such zones elastically extensible and/or to increase such elastic extensibility, respectively. Preferred activation treatments include, for example, MD or CD stretching, ring rolling, embossing, thermoforming, high pressure hydraulic forming or casting. Elastomeric laminates comprising at least one non-elastomeric skin layer and at least one core layer where the laminate is treated to exhibit preferential activation regions and non-preferential activation regions so that the preferential activation regions can be stretched to an elastic state, are disclosed in EP 0,521,388. This elastomeric laminate can be used in the support film 34 of the assembly 40 of the present invention.

The support film 34 may comprise further materials such as, for example, stiffening materials, coloured films, printings or registered marks. The support film 34 may also impart further functionalities such as breathability or differential stiffnesses to the assembly 40.

Stiffening materials include, for example, thermally or sonically structured surfaces or additional layers or coatings applied to the support film 34.

The support film 34 preferably has a Gurley stiffness value both in CD and MD as evaluated according to TAPPI Standard Test T 543 om-94, of less than about 1,000 milligrams (mg). The Gurley stiffness both in CD and MD preferably is less than 500 mg and especially preferably less than 200 mg.

The support films 34 suitable for use in the tape tab 27 of a diaper 20b or in a sanitary napkin 20a are described as illustrative examples of substrate 5 only but are not intended to be limiting in any way. The substrate 5 may be formed by any article or construction having an exposed surface capable of adhering to adhesive layer 6 of the fastening film system 1.

Figure 2A:
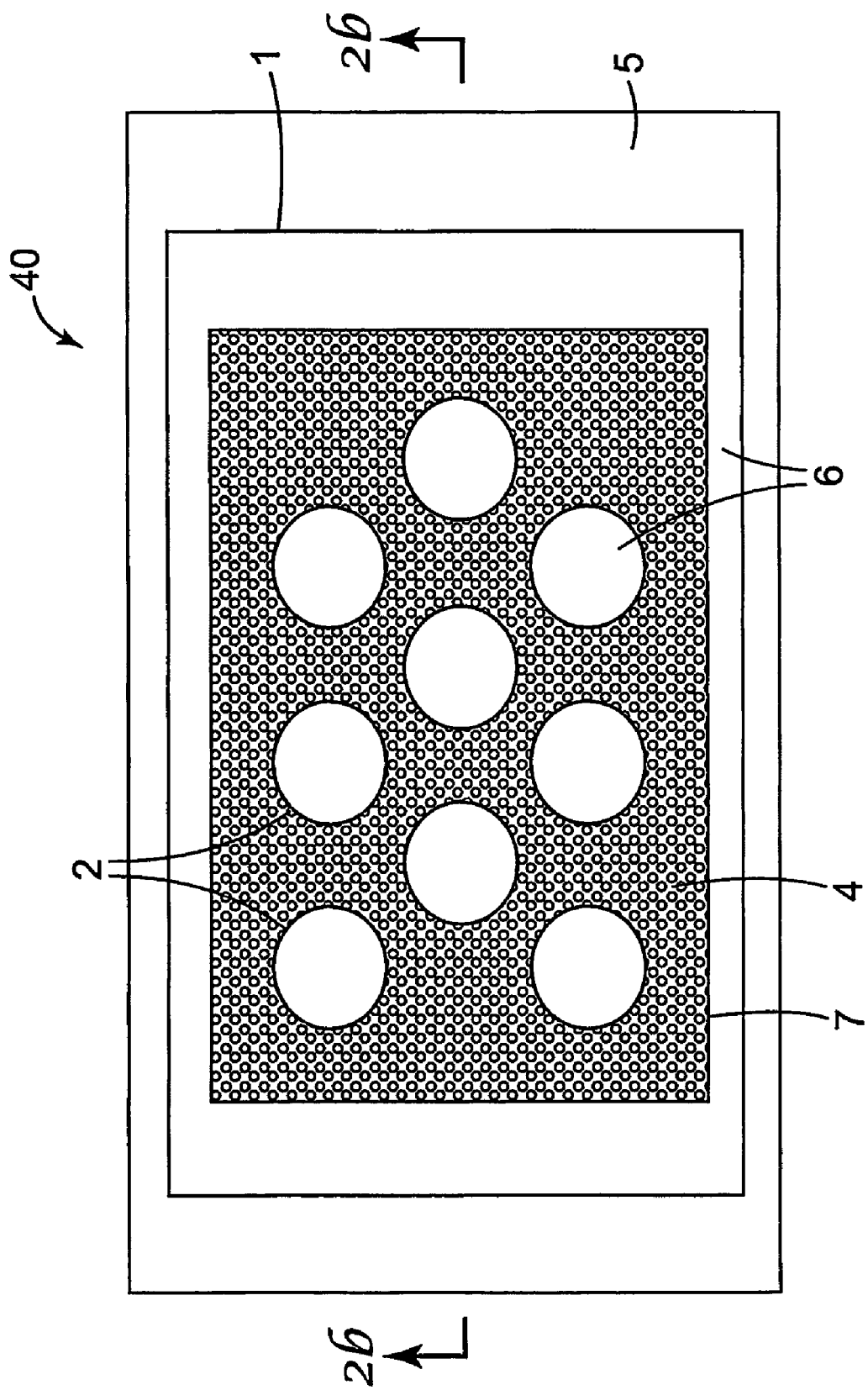
FIG. 2a is a top view of a preferred embodiment of an assembly 40 of the present invention.
Figure 2B:
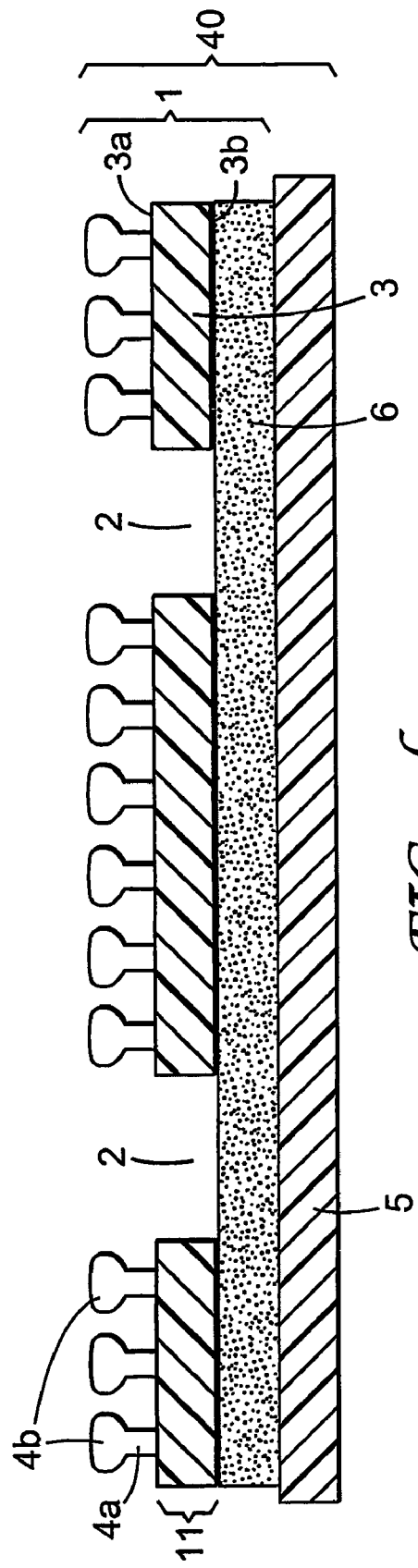

The dimensions of the substrate 5 in CD and/or MD may essentially match with the corresponding dimensions of the backing 7 or the fastening film system 1 but it is also possible that the dimensions of the substrate 5 in CD and/or MD differ from and, in particular, exceed the corresponding dimensions of the backing 7 or the fastening film system 1 as is shown, for example, in FIGS. 2a and 2b.

The fastening film systems 1 according to the present invention may be obtained by several methods. In the first step of a first embodiment of such method, a backing 7 bearing a plurality of male fastening elements 4 is provided. The male fastening elements 4 are preferably integral with the exposed major surface 3a of the backing 7. The manufacture of such backings is disclosed, for example, in U.S. Pat. Nos. 5,077,870, 5,679,302 and U.S. Pat. No. 4,894,060. Such backings 7 are also commercially available, for example, from 3M Company, St. Paul, Minn., USA, under the trade designations CS-200, CS-600 and CS-1010.

In the second step of such method, through-holes 2 are introduced into such backing, for example, by passing a continuous web of such backing 7 by a die-cutting station or between appropriately designed rotary cut knives. Any method of die-cutting, laser cutting or punching the through-holes 2 into the backing 7 can be applied.

In the third step of such method, an adhesive layer 6 such as an unsupported pressure-sensitive adhesive layer is provided and laminated to the major surface 3b of the backing 7 opposite to its exposed major surface 3a bearing the male fastening elements 4, thus providing a fastening film system 1 according to the present invention. The fastening film system 1 thus obtained can then be wound upon itself, optionally together with a siliconized release film, and stored in the form of a roll. The adhesive layer 6 preferably is an unsupported adhesive layer but it can also be formed by one of the two adhesive layers of a double-coated adhesive tape comprising a carrier film bearing two adhesive layers.

In the first step of a second embodiment of preparing fastening film systems 1, a backing 7 is provided bearing a plurality of male fastening elements 4.

In the second step of such method, one or more continuous cuts 8 are applied in MD to the backing 7. The cuts which can be applied to the backing 7 by passing it between rotary cut knives, are periodic and exhibit a wavelength 8a and an amplitude 8b as is shown, for example, in FIG. 3a. The shape of the notches 9 and protrusions 10 thus obtained, can vary broadly and preferred embodiments include, for example, sinusoid shapes or a regular sequence of rectangular or trapezoid notches 9 and protrusions 10. A regular sequence of trapezoid incisions is depicted, for example, in FIG. 3a. It is also possible that the notches 9 and protrusions exhibit a more complicated shape comprising two or more sub-notches and/or two or more sub-protrusions.

In the third step of such method, two adjacent sub-backings 7a, 7b provided by such continuous cuts 8 are separated by a distance exceeding the maximum amplitude 8b in the CD and by a distance essentially equal to half of the wavelength 8a/2 or a multiple of 8a/2, respectively, in the MD. The number of sub-backings 7a, 7b obtained depends on the number of cuts 8 which are applied to the backing 7. Since an even number of sub-backings is required, i.e. 2, 4, 6, etc. sub-backings 7a, 7b, an odd number of cuts 8, i.e. 1, 3, 5, etc. cuts 8, needs to be applied correspondingly.

Figure 3A:
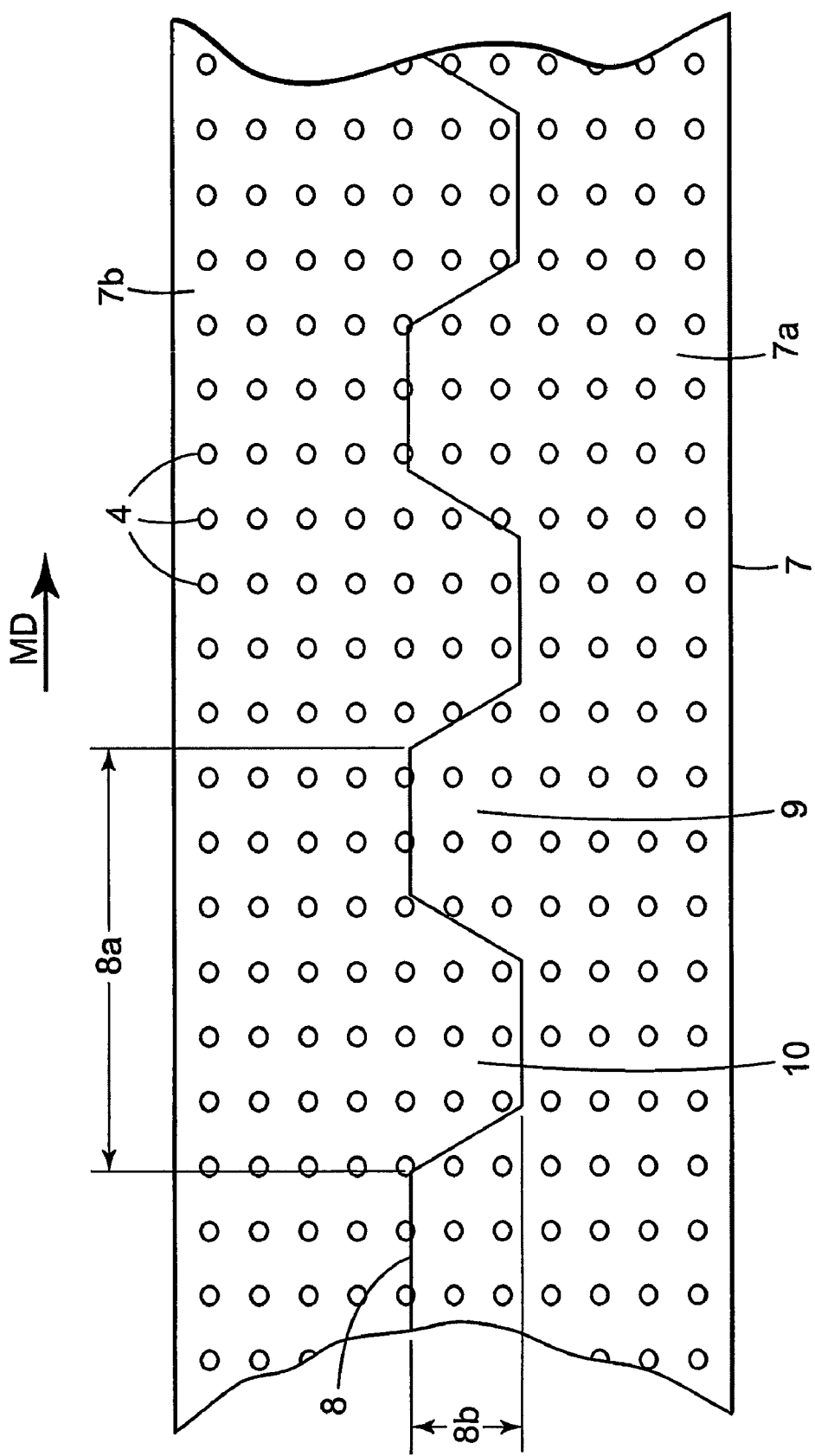
FIGS. 3a-3d schematically illustrate a preferred method of preparing a fastening film system 1 of the present invention.
Figure 3B:
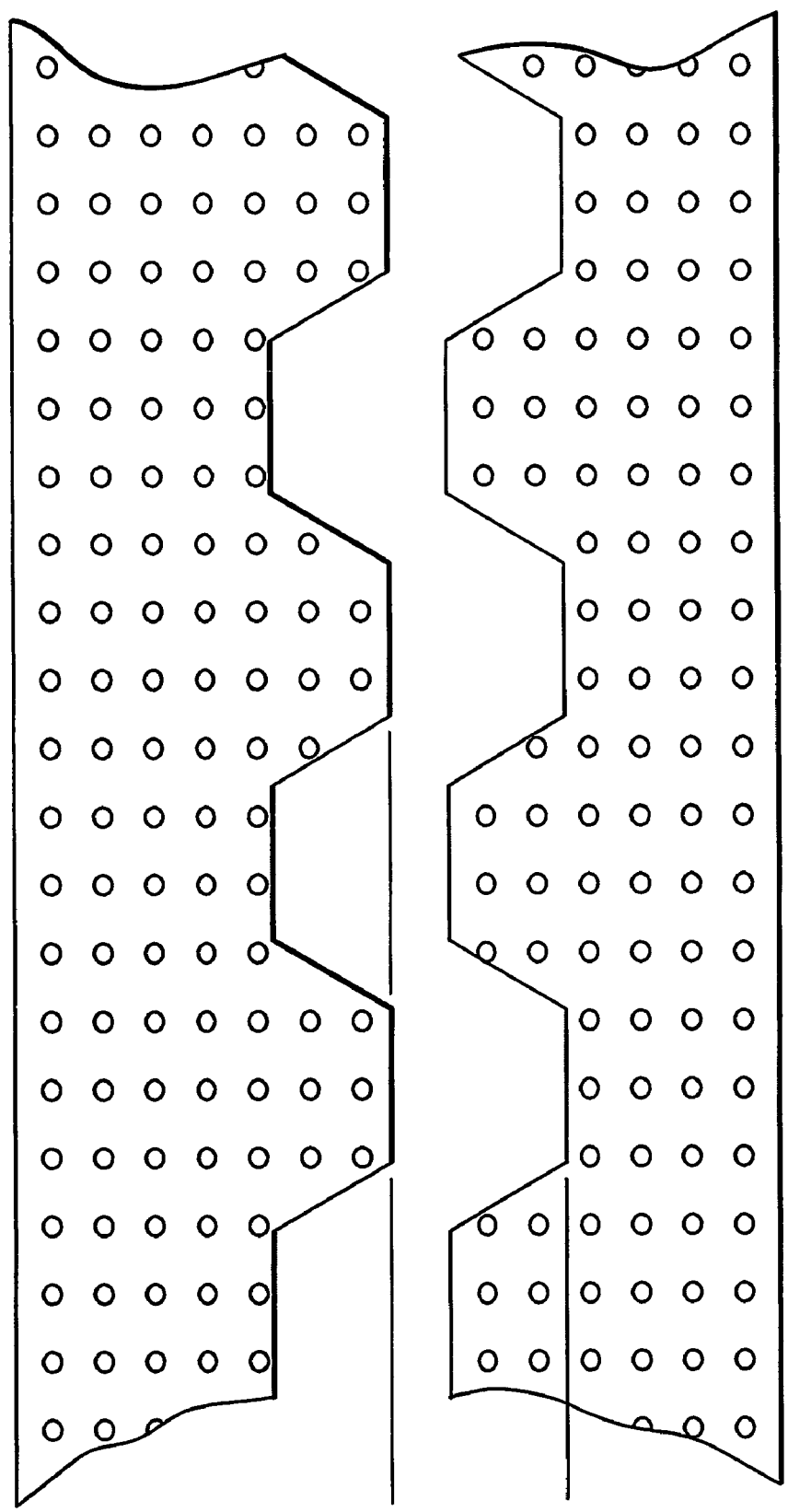
Figure 3C:
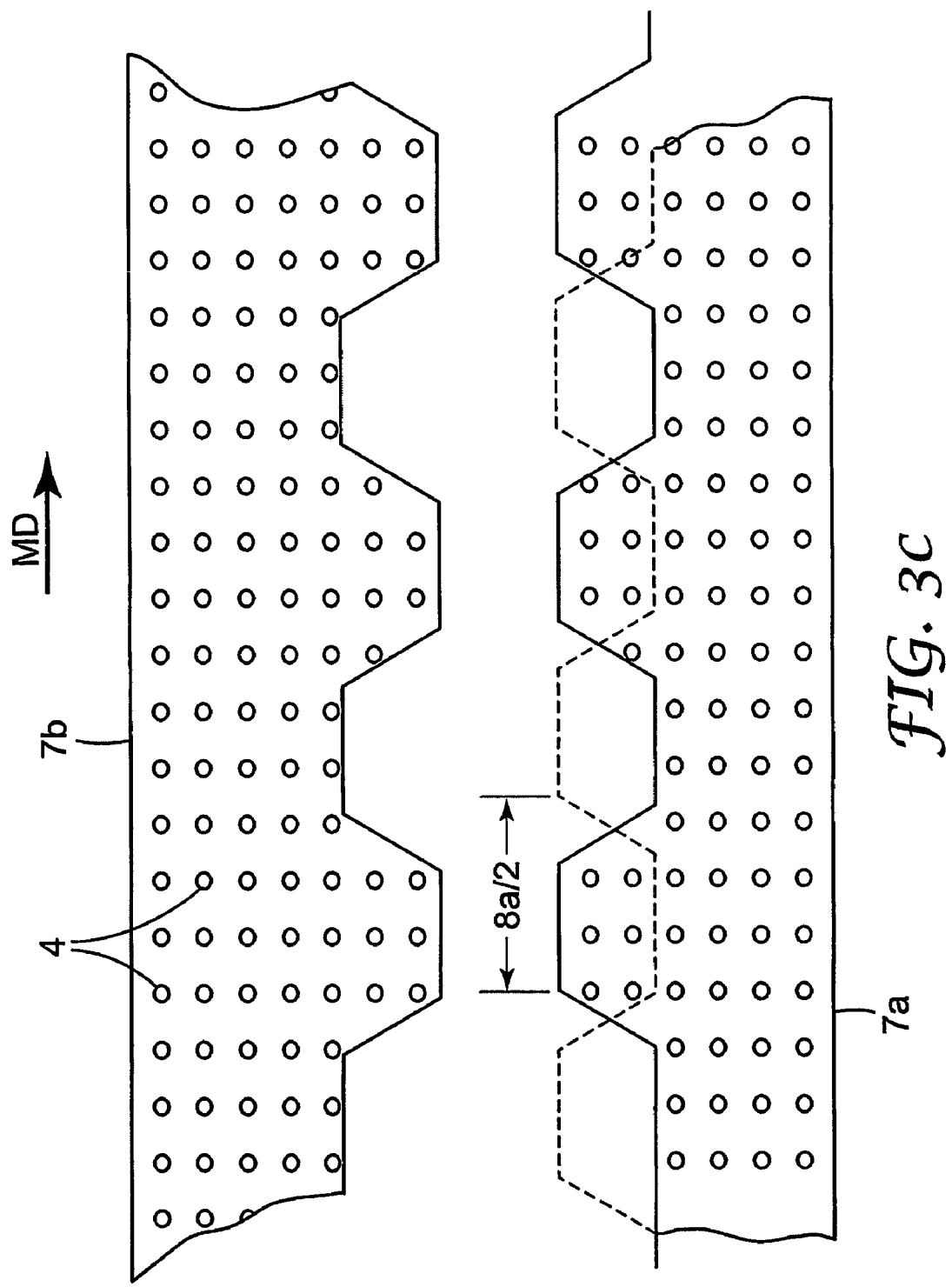
Figure 3D:
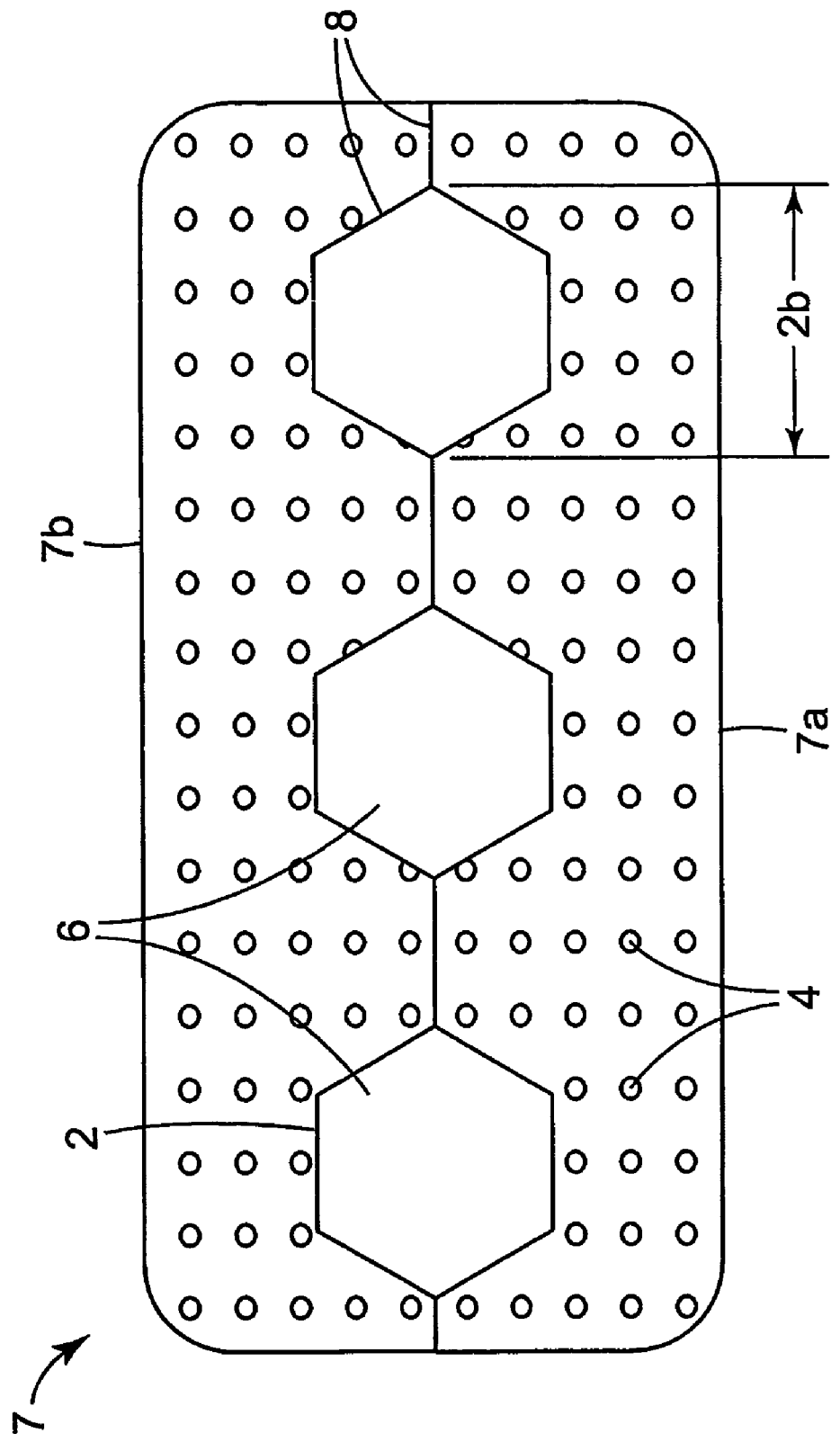

When shifting two adjacent sub-backings 7a, 7b towards each other in CD, through-holes 2 are formed which may be essentially completely encompassed by the backing as is schematically illustrated in FIG. 3d. Depending on the shape of the notches 9 and protrusions 10, it is, for example, also possible to provide a sequence of completely encompassed and not completely encompassed through-holes 2, respectively.

In the fourth step of such method, two adjacent sub-backings 7a, 7b as obtained in step 3 are laminated to an adhesive layer 6 so that through-holes are formed which are at least partly encompassed by the backing 7. A piece of the resulting fastening film system 1 obtained by cutting the sub-backings 7a, 7b in CD is shown in FIG. 3d.

The assembly 40 of the present invention comprising a fastening film system 1 and a substrate 5 may be obtained by several methods.

In the first step of a first method of preparing an assembly 40, an adhesive layer 6 is applied to an exposed surface of the substrate 5. The adhesive layer 6 may be applied, for example, by coating or spray-coating a solution of the adhesive in an appropriate solvent such as, water, MEK or aceton with subsequent drying. It is also possible to coat a partially cured precursor of the adhesive which preferably is solvent-free, to such exposed surface of the substrate 5 with subsequent curing, optionally in an inert atmosphere of nitrogen and/or argon, for example. The degree of polymerization of the precursor is selected to provide for an appropriate coating viscosity as is disclosed, for example, in U.S. Pat. No. 4,181,752. It is also possible to apply the adhesive layer 6 by hot-melt coating, screenprinting, rotary screenprinting or by lamination of an adhesive layer. The adhesive layer 6 preferably is an unsupported adhesive layer but it can also be formed by one of the two adhesive layers of a double-coated adhesive tape comprising a carrier film bearing two adhesive layers.

The dimensions of the adhesive layer 6 in CD and/or MD may essentially match with the corresponding dimensions of the backing 7 but it is also possible that the dimensions of the adhesive layer 6 in CD and/or MD differ and, in particular, exceed the dimensions of the backing 7. The assemblies 40 shown in FIGS. 2a and 2b and in FIG. 6b, for example, comprise adhesive layers 6 the dimensions of which exceed the dimensions of the corresponding backing 7.

In the second step of such method, a backing 7 bearing on one of its major surfaces a plurality of male fastening elements 4 is provided.

The male fastening elements 4 are preferably integral with the exposed major surface of the backing 7. The manufacture of such backings is disclosed, for example, in U.S. Pat. Nos. 5,077,870, 5,679,302 and U.S. Pat. No. 4,894,060. Such backings 7 are also commercially available, for example, from 3M Company, St. Paul, Minn., USA, under the trade designations CS-200, CS-600 and CS-1010.

In the third step of such method, through-holes 2 are introduced into such backing 7, for example, by passing a continuous web of such backing 7 by a die-cutting station or between appropriately designed rotary cut knives. Any method of die cutting, laser cutting or punching the through-holes 2 into the backing 7 can be applied.

In the fourth step of such method, the backing 7 comprising through-holes 2 is attached with its major surface 3b which is opposite to its major surface 3a bearing a plurality of male fastening elements 4, to the exposed surface of adhesive layer 6. The assembly 40 thus obtained comprises a fastening film system 1 comprising a backing 7 with through-holes 2 and an adhesive layer 6, and a substrate 5.

In the first step of a second method of preparing an assembly 40, a fastening film system 1 is prepared by any of the methods disclosed above and attached in a second step of such method through the exposed surface of the adhesive layer 6 to an exposed surface of the substrate 5.

From the above methods of preparing fastening film systems 1 and assemblies 40, respectively, the first method of preparing an assembly 40 which includes applying of an adhesive layer 6 to an exposed surface of the substrate 5 with subsequent application of a backing 7 having through-holes 2 through the major surface 3b of the backing 7, to the exposed surface of the adhesive layer 6, is especially preferred. A backing 7 comprising through-holes 2 is especially preferably obtained by the methods exemplified in FIG. 3a-3d.

The fastening film system 1 and the assemblies 40, respectively, obtained in any of the preceding methods provide a combination of an adhesive and a mechanical bonding mechanism when brought into contact with fibrous materials 32. Fibrous materials 32 exhibit a structure comprising loops, tangled fibers or openings which form female bonding elements with which the male bonding elements 4 on the exposed major surface of the backing 7 of the fastening film system 1 can interact.

Fibrous materials 32 which are especially preferred for use in the present invention include woven, knitted and nonwoven materials and mixed fabrics comprising any of the preceding materials. The fibrous material 32 preferably has a basis weight of less than 350 g/m$^2$, more preferably of less than 300 g/m$^2$ and especially preferably of less than 250 g/m$^2$. The fibrous material 32 may comprise materials which are selected from a group comprising cotton, nylon, silk, polyester and polyethylenes such as polypropylene.

Suitable processes for making webs of nonwoven materials include but are not limited to airlaying, spunbonding, spunlacing, bonding of melt blown web and bonding of carded webs.

Spunbond nonwoven webs are made by extruding a molten thermoplastic as filaments from a series of fine die orifices in a spinneret. The diameter of the extruded filaments is rapidly reduced under tension by, for example, non-eductive or eductive fluid-drawing or other known spunbond mechanisms, such as described in U.S. Pat. Nos. 4,340,563, 3,692,618, 3,338,992, 3,341,394, 3,276,944, 3,502,538, 3,502,763 and U.S. Pat. No. 3,542,615. The spunbond web is preferably bonded (point or continuous bonding).

The nonwoven web layer may also be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation. Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Meltblown webs may be formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength, meltblown webs must be further bonded such as by through air bonding, heat or ultrasonic bonding as described above.

The fibrous material 32 which may be used in the landing zone 28 of diapers 20b comprises, for example, knitted loop, velour-type loop or extrusion-bonded nonwoven loop materials. Such materials are commercially available from 3M Company, St Paul, Minn., USA.

Undergarments and pieces of underwear 31 typically comprise fibrous materials 32 which may be woven, knitted or nonwoven. The fibrous materials used in undergarments include, for example, cotton, silk, nylon, polyester and polyolefin such as polypropylene.

It was surprisingly found that the fastening film system 1 and the assembly 40 of the present invention exhibit an advantageous balance of the adhesive and mechanical bonding mechanism to a variety of fibrous materials 32.

The term "mechanical bonding mechanism" as used above and below includes any interaction between the male fastening elements 4 arranged on the major surface 3a of the backing 7, and the fibrous material 32 including, for example, 90° peel adhesion, hang shear adhesion or any frictional interaction.

The term "adhesive bonding mechanism" as used above and below includes any interaction between the adhesive layer 6 exposed through the through-holes 2, and the fibrous material 32 including, for example, 90° peel adhesion, hang shear adhesion and any frictional interaction.

The fastening film systems 1 of the present invention can preferably be employed in disposable absorbent articles 20 such as, for example, sanitary napkins 20a or diapers 20b.

The term sanitary napkin 20a as used above and below refers to an article which is worn by females adjacent to the pudential region that is intended to absorb and contain the various exudates which are discharged from the body (e.g. blood, menses and urine). The term sanitary napkin 20a is also meant to include light weight incontinence pads for adults. Sanitary napkins 20a typically have a top sheet 21 which provides a liquid pervious body-contacting surface and a back sheet 22 which provides a liquid impervious garment surface. The top sheet 21 and the back sheet 22 sandwich an absorbent core 23 providing the means for absorbing menses and other body fluids. The top sheet 21 is intended to be worn adjacent to the body of the wearer. The back sheet 22 of the sanitary napkin is on the opposite side and is intended to be placed adjacent to the wearer's undergarments when the sanitary napkin 20a is worn.

Constructions of sanitary napkins 20a are described in detail, for example, in U.S. Pat. No. 5,611,790, WO 98/53,782, U.S. Pat. Nos. 5,778,457, 6,039,712, WO 98/53,781, U.S. Pat. Nos. 4,336,804, 4,475,913, 6,443,932 and U.S. Pat. No. 5,507,735.

The present invention, however, is not limited to the particular types or configurations of sanitary napkins 20a described in the above references.

The sanitary napkins 20a according to the present invention differ from prior art constructions in that one or more fastening film systems 1 or assemblies 40, respectively, are applied to the back sheet 22 and/or other parts of the sanitary napkin 20a, such as the side wrapping elements 30 contacting the wearer's undergarments during use. In a preferred embodiment, an adhesive layer 6 is applied to the back sheet 22 of the sanitary napkin 20a which forms a substrate 5. Subsequently, a backing 7 comprising through-holes 2 is attached through its major surface 3b to the adhesive layer 6 thereby forming an assembly 40 comprising the sanitary napkin as a substrate 5, and the adhesive layer 6 and backing 7 as a fastening film system 1. The ratio of the exposed major surface 3a of the backing 7 relative to the surface area of the backing 7 and/or the side wrapping element 30 preferably is between 0.15 and 1.0 and more preferably between 0.25 and 1.0.

The fastening film system 1 provides an attachment means for securing the sanitary napkin 20a to the wearer's undergarments or panties during use. It was surprisingly found that sanitary napkins 20a according to the present invention can be reliably secured to a variety of undergarments comprising various fibrous materials 32 such as woven, knitted or non-woven materials comprising, for example, cotton, silk, nylon, polyester, polyolefin such as polypropylene or a mixture of any of the preceding material. The sanitary napkins 20a of the present invention develop a good overall bond strength to a variety of fibrous materials 32 and simultaneously exhibit a good balance of the adhesive and mechanical bonding mechanism so that the sanitary napkin 20a is reliably secured to various types of undergarments without damaging, for example, undergarments with—compared to cotton based materials—a relatively low degree of loftiness by an excessive adhesive bonding strength. Materials with a relatively low degree of loftiness include, for example, silk or nylon based materials whereas cotton based materials typically have a higher degree of loftiness. The loftiness of a fibrous material depends on various parameters including the type and physical characteristics of its fibers and/or filaments and the method of web forming.

The sanitary napkins 20a of the present invention are thus characterized by an increased wearer's comfort. Due to the advantageous balance of adhesive and mechanical bonding properties of the fastening film systems 1 and assemblies 40 of the present invention, the sanitary napkins 20a can also be stacked upon each other without requiring, for example, a release-treated interlayer.

The fastening film system 1 of the present invention can also be used in disposable absorbent incontinence articles such as diapers 20b. Incontinence articles and diapers may have any desired shape such as, for example, a rectangular shape, an I shape, a T shape or an essentially hourglass shape.

Figure 6A:
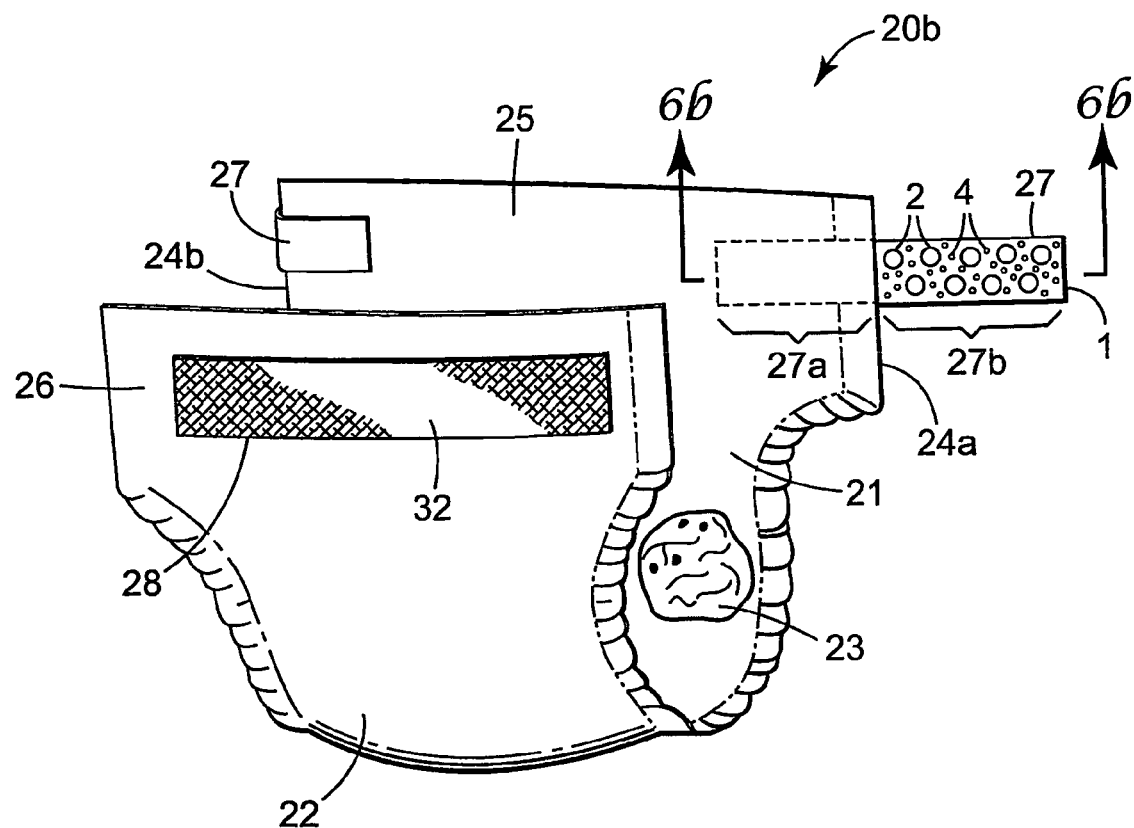
FIG. 6a is a schematic exploded view of a specific embodiment of a diaper 20b.

FIG. 6a is a schematic exploded view of a specific embodiment of a diaper 20b having an essentially hourglass shape. The diaper comprises an absorbent core between a liquid pervious top sheet 21 contacting the wearer's skin, and a liquid impervious back sheet 22 facing outwardly. The diaper 20b has a first end region 25 having two tape tabs 27 arranged at the two longitudinal edges 24a, 24b of the diaper 20b. The tape tabs 27 are secured through their manufacturer's end 27a to the first end region 25. When attaching the diaper 20b to a wearer's body, the user's ends 27b of the tape tabs 27 each comprising a fastening film system 1 of the present invention are attached to the target area 28 comprising fibrous material 32 which may be arranged on the back sheet 22 of the second end region 26. Examples of loop tapes which may be applied to the target area 28 to provide an exposed fibrous material, are disclosed, for example, in EP 0,754,415, EP 0,693,889, EP 0,341,998 and EP 0,539,504. In an alternative construction, the back sheet 22 comprises a woven or non-woven fibrous layer which is capable of interacting with the user's ends 27b of the tape tabs 27 each comprising a fastening film system 1 or assembly 40 of the present invention so that no separate target area is required. Such back sheets 22 are disclosed, for example, in U.S. Pat. No. 6,190,758 and U.S. Pat. No. 6,075,179.

Figure 6B:
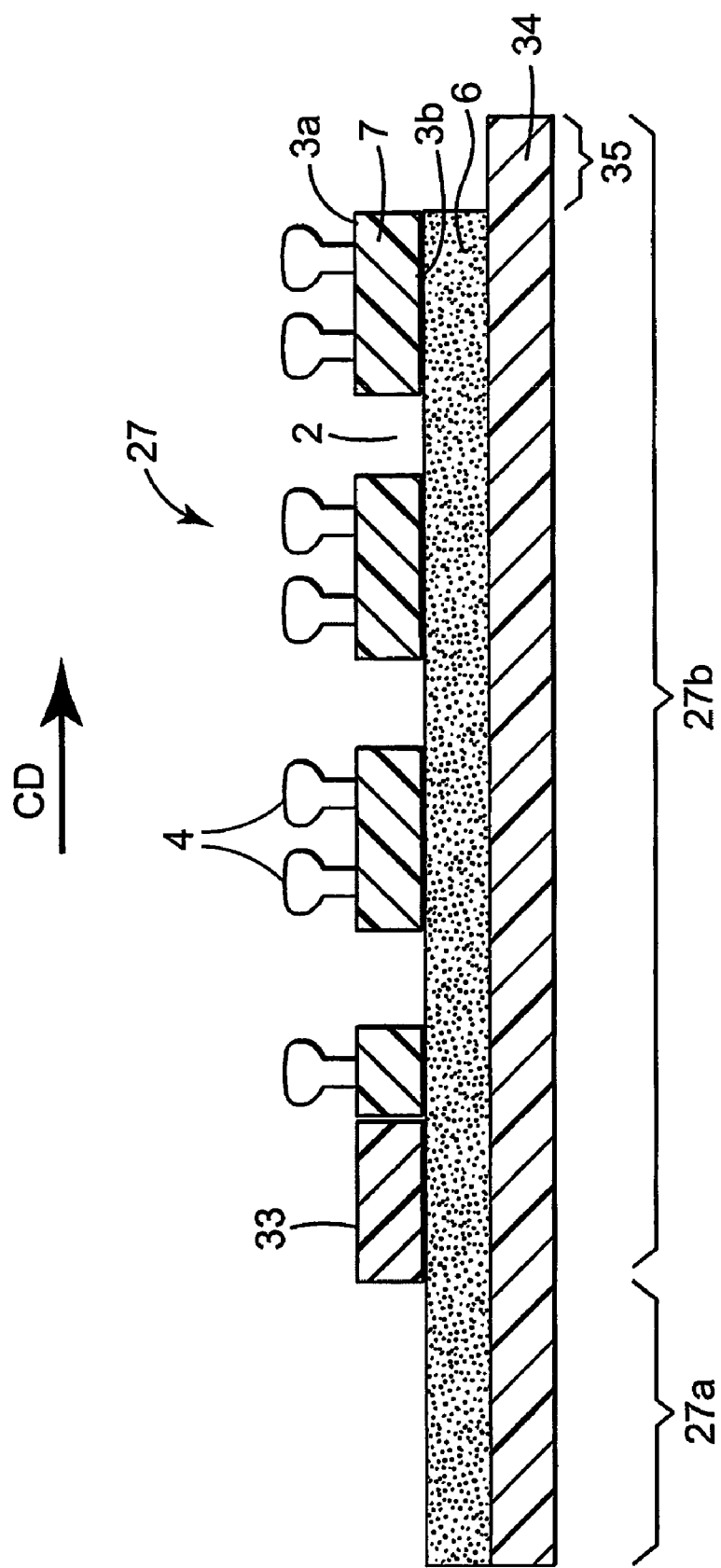
Figure 6C:
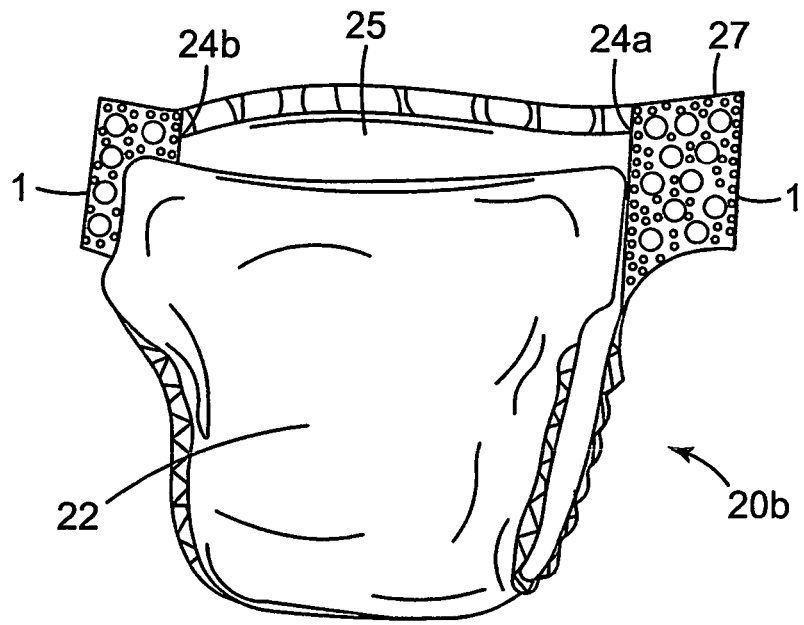
FIG. 6c is a schematic exploded view of a specific embodiment of a diaper 20b.

FIG. 6c is a schematic exploded view of another preferred embodiment of a diaper 20b where a large area tape tab 27 is used comprising a fastening film system 1 of the present invention. In the construction of FIG. 6c the back sheet 22 is capable of interacting with the fastening film system 1 via a combination of a mechanical and an adhesive bonding mechanism so that a separate target area 28 is not required.

Figure 6D:
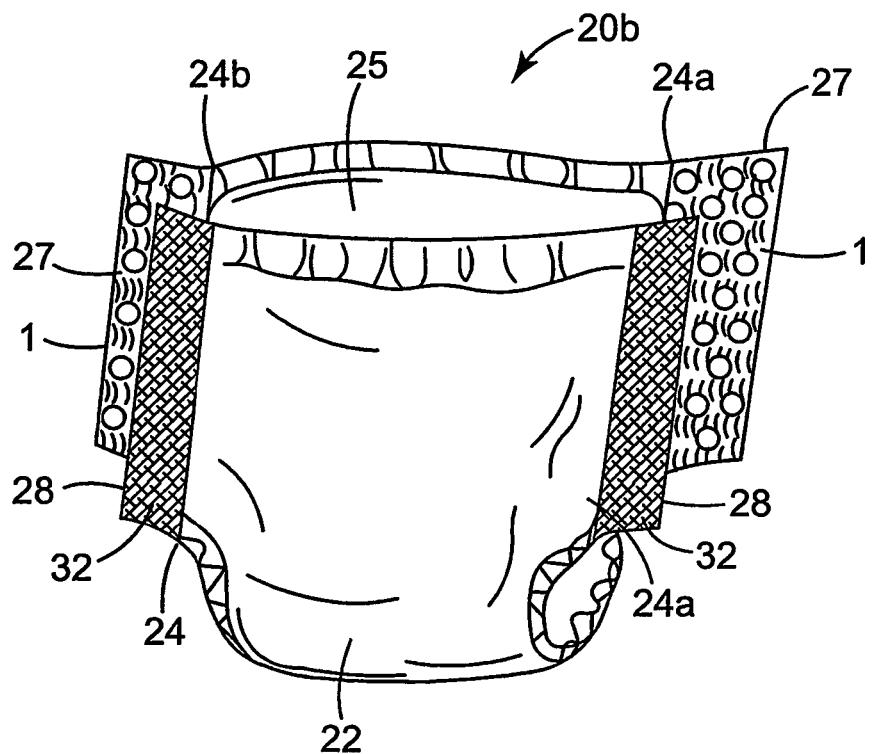
FIG. 6d is a schematic exploded view of a specific embodiment of a diaper 20b.

FIG. 6d shows a schematic exploded view of another specific embodiment of a diaper 20b where a large area tape tab 27 comprising a fastening film system 1 is used in conjunction with two landing zones 28 comprising a fibrous material 32. The tape tab 27 and the target areas 28 are arranged along the longitudinal edges 24a, 24b of the first and second end region 25, 26.

The tape tab 27 allows to releasably and refastenably attach the diaper 20b around the wearer's body. FIG. 6b shows a schematic cross-section of tape tab 27 comprising a manufacturer's end 27a for securing it to the diaper 20b and a user's end 27b comprising the fastening film system 1 or the assembly 40, respectively. The user's end is gripped by the user when attaching the diaper 20b to the wearer. The manufacturer's end 27a corresponds to the part of the tape tab 27 which is fixed or secured to the diaper 20b during the manufacture of the diaper 20b; it usually extends from one of the lateral edges (i.e. the edges in cross-direction) of the tape tab 27 to the longitudinal edges 24a, 24b of the diaper 20b. The user's end 27b corresponds to the part of the tape tab 27 which is not anchored to the diaper 20b during manufacture; it usually corresponds to the part of the tape tab 27 which is different from the manufacturer's end 27a.

During manufacturing or when the diaper 20b is stored prior to use, the user's end 27b of the tape tab 27 is usually folded over onto the top sheet 21 as is shown, for example, tor one of the two tape tabs 27 in the diaper 20b of FIG. 6a. It is important during the manufacturing of the diaper 20b that the user's end 27b does not pop open but is releasably secured to the top sheet 21 of the diaper 20b. This so-called "anti-flagging feature" of the tape tab 27 is provided by the exposed surface of the fastening film system 1 or assembly 40 of the tape tab 27 which provides a combination of a mechanical and an adhesive bonding mechanism. When the diaper 20b has been used or soiled, it is typically rolled up after use and discarded whereby it is convenient to secure the diaper 20b in the rolled-up state to avoid spillage of excrements. This so-called "disposal feature" is also provided by the exposed surface of the fastening film system 1 or the assembly 40 of the tape tab 27 which provides a combination of a mechanical and an adhesive bonding mechanism.

The tape tab 27 may comprise a support film 34 in addition to the fastening film system 1, which may bear, be bonded to or integrally include, respectively, functional components such as, for example, elastic means, fingerlifts, release tapes to provide a Y-bond between the diaper 20b and the tape tab 27, or cover films 33. The support film 34 and the functional components attached to or incorporated into it, respectively, are selected to impart advantageous properties such as, for example, elasticity, breathability or differential stiffness in machine or cross-direction, respectively, to the tape tab 27. The support film 34 is described above in same detail.

Further details on diapers 20b and their construction are described in literature and may be taken, for example, from U.S. Pat. No. 5,399,219, WO 96/10,382 or EP 0,529,681. Examples for the construction of tape tabs 27 are given, for example, in WO 99/03,437, EP 0,321,232 or U.S. Pat. No. 5,399,219.

The diaper 20b of the present invention differs from prior art constructions in that the user's end 27b of the tape tab 27 comprises a fastening film system 1. In a preferred embodiment, an adhesive layer 6 is applied to the support film 34 which forms a substrate 5. Subsequently, a backing 7 comprising through-holes 2 is attached through its major surface 3b to the adhesive layer 6 thereby forming an assembly 40 comprising the support film 34 as a substrate 5, and the adhesive layer 6 and the backing 7 as a fastening film system 1.

It was found that the tape tab 27 of the present invention has an advantageous combination of an adhesive and mechanical bonding mechanism so that it can be repeatedly opened and re-affixed essentially without damaging the fibrous material 32 arranged, for example, on the landing zone 28 or on the back sheet 22, respectively.

DETAILED DESCRIPTION OF THE FIGURES

FIG. 1a shows the top view of a fastening film system 1 comprising a backing 7 bearing on its exposed major surface 3a a plurality of male fastening elements 4 and exhibiting a plurality of through-holes 2 at least part of which are fully encompassed by the backing 7. The backing 7 furthermore bears on its major surface 3b opposite to said exposed major surface 3a an adhesive layer 6 which is exposed in the areas of the through-holes 2.

FIG. 1b is a cross-section along the line 1b-1b through the fastening film system 1 of FIG. 1a. The fastening film system 1 comprises a backing 7 exhibiting on its major surface 3b which is opposite to the exposed major surface 3a of the backing, a continuous adhesive layer 6. The backing 7 comprises on its exposed major surface 3a a multitude of mushroom-type male fastening elements 4 each comprising a stem 4a supported by the backing 7 and an enlarged section 4b at the end of the stem 4a opposite to the backing 7. The backing furthermore exhibits through-holes 2 through which the adhesive layer 6 is exposed.

FIG. 1c is a reproduction of FIG. 1a which additionally comprises two auxiliary dotted lines which are used to determine the maximum number of through-holes 2 of the piece of fastening film system 1 of FIG. 1 in the CD and in the MD.

FIG. 1d shows the top view of a fastening film system 1 comprising two pieces of backing 7, 7' bearing on their exposed major surfaces 3a a plurality of male fastening elements 4 and exhibiting a plurality of through-holes 2. The backing 7, 7' furthermore bears on its major surface 3b opposite to said exposed major surface 3a an adhesive layer 6 which is exposed in the areas of the through-holes 2. The fastening film system 1 comprises through-holes 2 which are fully encompassed by the backing 7, 7' and also—at the edge of the backing 7, 7' and as a strip of exposed adhesive between the two backings 7,7'—through-holes 2 which are not fully encompassed by the backing 7, 7'.

FIG. 2a shows the top view of an assembly 40 of the present invention comprising a fastening film system 1 and a substrate 5. The fastening film system 1 comprises a backing 7 exhibiting on its exposed major surface 3a a plurality of male fastening elements 4 and having a plurality of through-holes 2. An adhesive layer 6 is arranged on the major surface 3b of the backing 7 which is opposite to said exposed major surface 3a. The adhesive layer 6 is exposed in the area of the through-holes 2. The surface of the adhesive layer 6 which is opposite to the surface of the adhesive layer 6 exposed through through-holes 2, is attached to an exposed surface of a substrate 5. In the embodiment of FIG. 2a, the dimensions of the adhesive layer 6 exceed the dimensions of the backing 7 and the dimensions of the substrate 5 exceed the dimensions of both the adhesive layer 6 and the backing 7.

FIG. 2b is a cross-section along the line 2b-2b through the assembly 40 of FIG. 2a.

FIG. 3a shows the top view of a backing 7 extending continuously in MD which bears a plurality of male fastening elements 4. A periodic cut 8 having a wavelength 8a and an amplitude 8b has been provided in MD thereby creating a sequence of notches 9 and protrusions 10, respectively, and separating the backing 7 into two sub-backings 7a and 7b.

FIG. 3b shows the top view of the two continuous sub-backings 7a, 7b of FIG. 3a which have been separated in CD by a distance which is greater than the amplitude 8b of the cut 8 (Δ>8b).

FIG. 3c shows the top view of the continuous sub-backings 7a, 7b of FIG. 3b whereby the sub-backing 7a has been shifted with respect to sub-backing 7b by half of the wavelength 8a/2 of the cut 8 in MD. The position of the sub-backing 7a prior to shifting is indicated in dotted lines.

FIG. 3d shows the top view of a piece of a continuous fastening film system 1 comprising the continuous sub-backings 7a, 7b of FIG. 3d whereby an adhesive layer 6 which is exposed through the through-holes 2, is attached to the major surface 3b of the backing 7 opposite to its exposed major surface 3a bearing the male fastening elements 4. The piece of the fastening film system 1 was obtained from the continuous web of the fastening film system 1 by cutting in CD.

Figure 4:
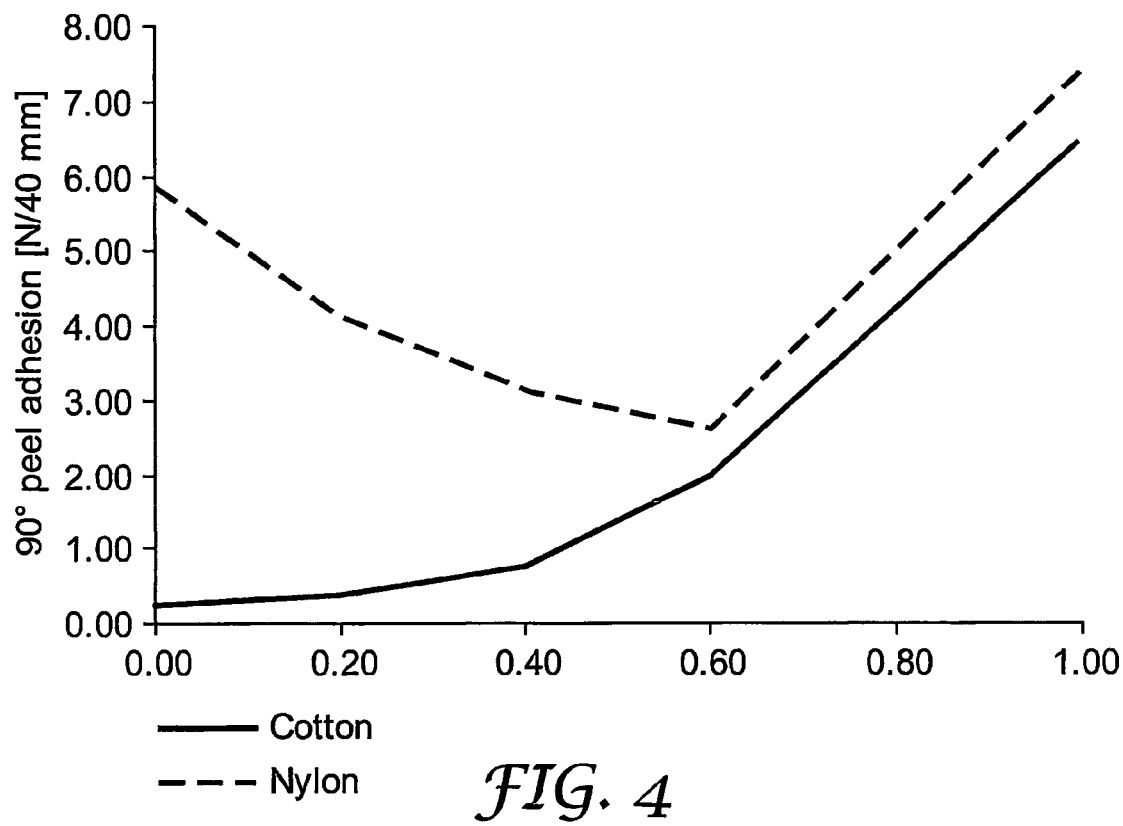
FIG. 4 is a plot of the average 90° peel adhesion vs. the ratio of the surface area of adhesive exposed through through-holes 2 over the surface area of the backing 7 of the assembly 40 obtained in Example 1.

FIG. 4 is a plot of the average 90° peel adhesion per 40 mm between the assembly 40 of Example 1 and a cotton and a nylon fabric, respectively, as a function of the ratio of the surface area of the through-holes 2 and the surface area of the backing 7 prior to applying through-holes 2. The surface area of the through-holes 2 corresponds to the surface area of the adhesive exposed through the through-holes 2.

Figure 5:
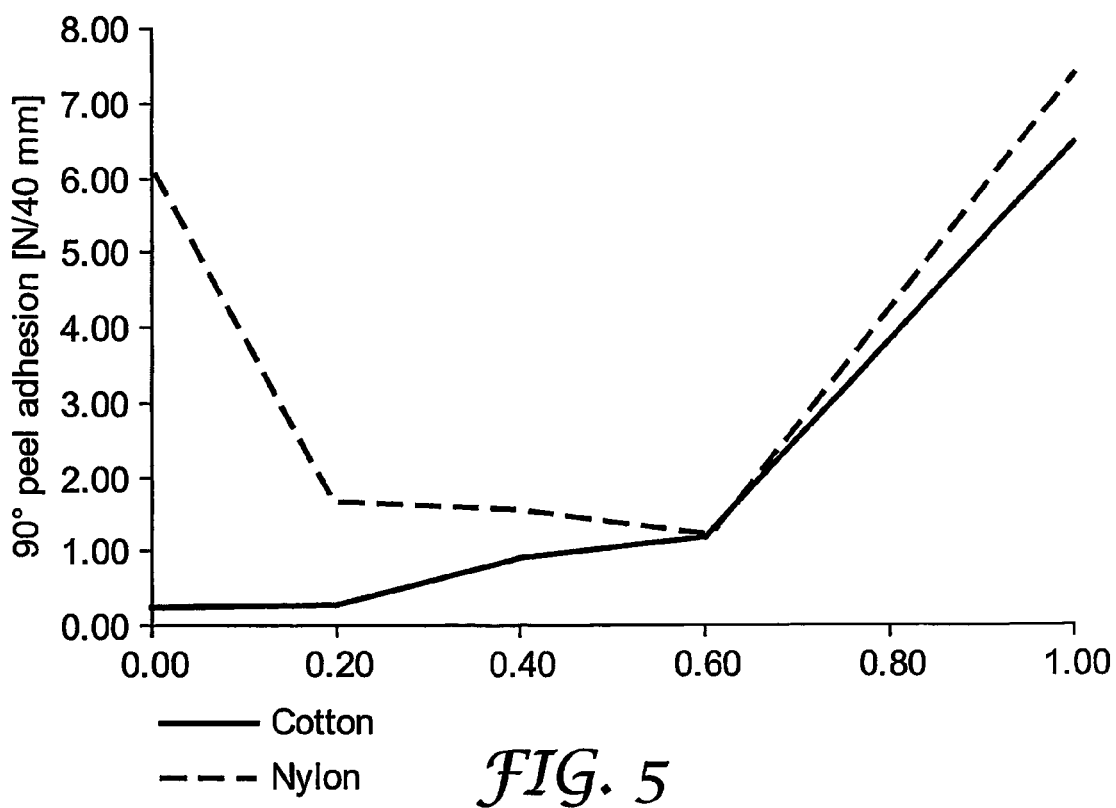
FIG. 5 is a plot of the average 90° peel adhesion vs. the ratio of the surface area of adhesive exposed through through-holes 2 over the surface area of the backing 7 of the assembly 40 obtained in Example 3.

FIG. 5 is a plot of the average 90° peel adhesion per inch between the assembly 40 of Example 3 and a cotton and a nylon fabric, respectively, as a function of the ratio of the surface area of the through-holes 2 and the surface area of the fastening film system 1. The surface area of the through-holes 2 corresponds to the surface area of the adhesive exposed through the through-holes 2.

FIG. 6a is a schematic exploded view of a disposable diaper 20b comprising a top sheet 21 and a back sheet 22 sandwiching an absorbent core 23. The diaper 20b has a first end region 25 comprising a pair of tape tabs 27 which are secured to the diaper 20b adjacent to longitudinal edges 24a, 24b and which comprise a fastening film system 1 having a plurality of male fastening elements 4 and through-holes 2. The diaper has a second end region 26 comprising a fibrous material 32 on the landing zone 28. The tape tabs 27 are secured to the diaper 20b through the manufacturer's end 27a while the user's end 27b is attached to the fibrous material 32 when securing the diaper 20b to the body of a wearer. The diaper 20b comprises an elastic material in the crotch region 29 (not shown).

FIG. 6b is a cross-section along the line 6b-6b through the tape tab 27 attached to the first end region 25 of the diaper 20b of FIG. 6a. The tape tab 27 comprises a support film 34 bearing adhesive layer 6 which is exposed at the manufacturer's end of the tape tab 27. At the user's end 27b of the tape tab 27, the adhesive layer bears a backing 7 comprising on its exposed major surface 3a a multitude of male fastening elements 4 and through-holes 2 through which the adhesive layer 6 is exposed. The backing 7 and the adhesive layer 6 form a fastening film system 1 of the present invention, and the backing 7, the adhesive layer 6 and the support film 34 form an assembly 40 of the present invention. The tape tab 27 furthermore optionally comprises a cover film 33 covering adhesive layer 6 in the remaining part of the user's end 27b adjacent to the manufacturer's end 27a. The outer end of the support film 34 at the user's end exceeds the extension of the backing 7 and the adhesive layer 6 thereby providing a fingerlift 35.

FIG. 6c is a schematic exploded view of another preferred embodiment of a diaper 20b comprising two large area tape tabs 27 which are arranged along the longitudinal edges 24a, 24b of the first end region 25 of the diaper. The tape tabs 27 comprise a fastening film system 1 of the present invention which interacts with the back sheet 22 of the diaper 20b comprising an exposed fibrous material.

FIG. 6d is a schematic exploded view of another preferred embodiment of a diaper 20b comprising two large area tape tabs 27 each comprising a fastening film system 1 of the present invention, and two target areas 28 each comprising an exposed fibrous material 32. The tape tabs and the target areas 28, respectively, are arranged along the longitudinal edges 24a, 24b of the diaper 20b.

Figure 7A:
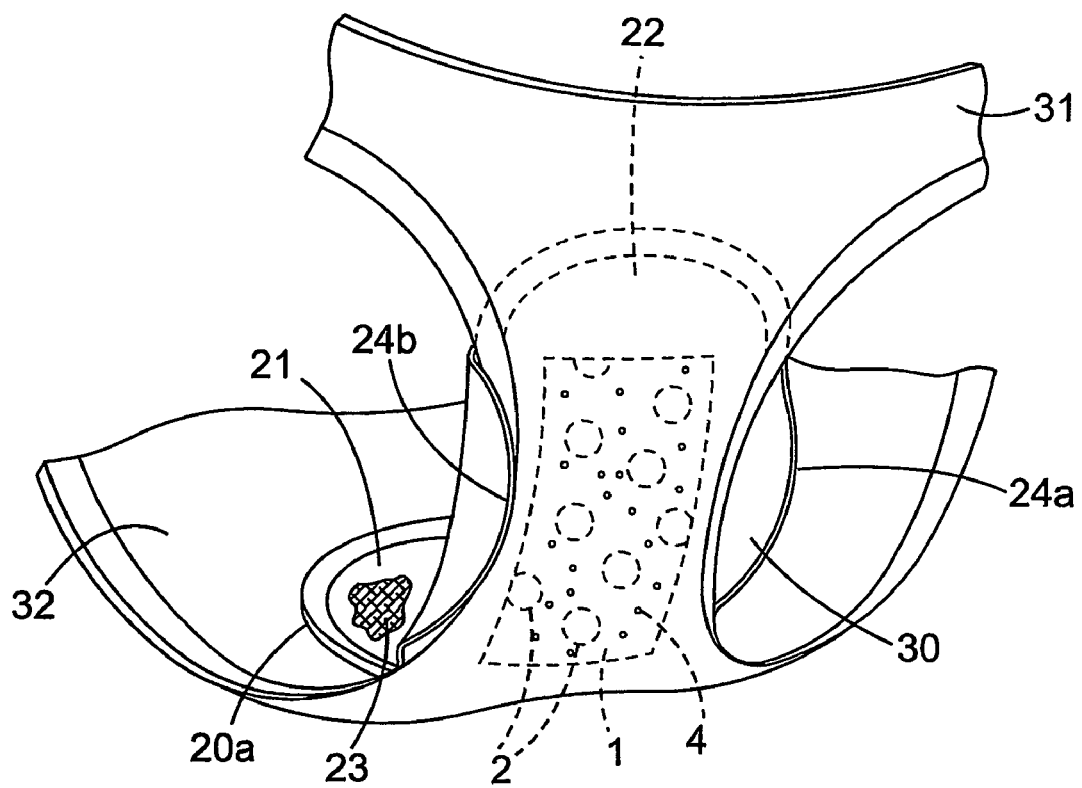

FIG. 7a is a schematic exploded view of a disposable sanitary napkin 20a being attached to a piece of undergarment 31. The napkin 20a has a liquid pervious top sheet 21 and a liquid impervious back sheet 22 sandwiching an absorbent core 23. The napkin 20a furthermore comprises side wrapping elements 30 adjacent to its longitudinal edges 24a, 24b which can be folded over when applying the napkin 20a to the wearer's piece of underwear 31. A fastening film system 1 comprising a multitude of through-holes 2 and mechanical fastening elements 4 is arranged on the back sheet 22 of the sanitary napkin 20a so that the major surface 3a of the backing 7 is exposed. The sanitary napkin 20a, the adhesive layer 6 and the backing 7 comprising through-holes 2 form an assembly 40 of the invention.

Figure 7B:
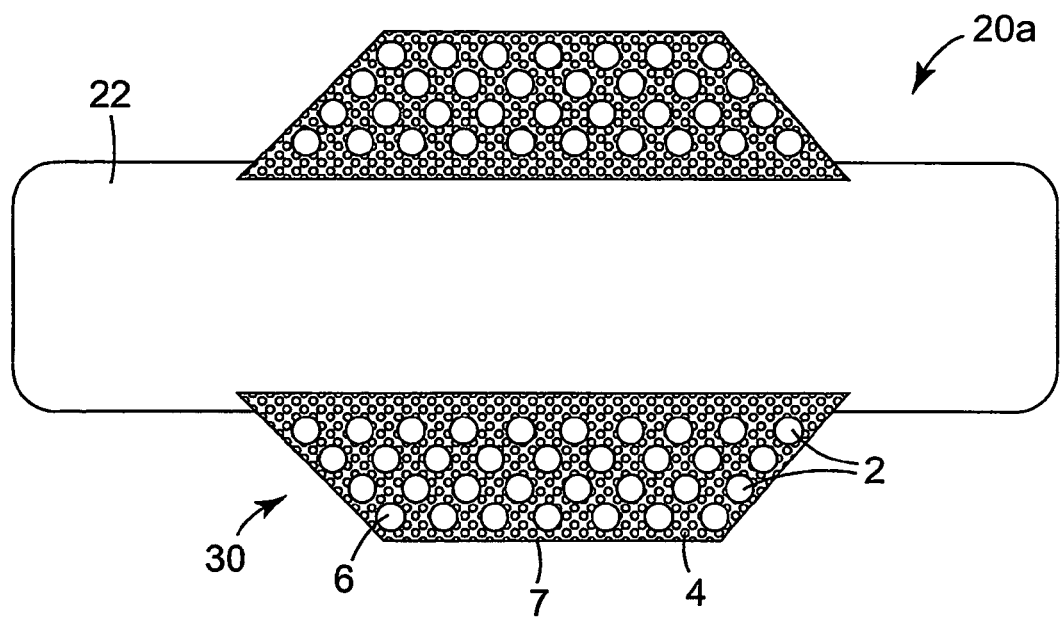

FIG. 7b is a schematic top view of a specific embodiment of a sanitary napkin 20a comprising side wrapping elements 30 attached to the back sheet 22 of the sanitary napkin 20a. The wrapping elements each bear on their garment side fastening film system 1 comprising a backing 7 and an adhesive layer 6 which is exposed through the through-holes 2 of the backing 7. The backing 7 furthermore comprises a multitude of male fastening elements 4 which are arranged on the exposed surface 3a of the backing 7.

Figure 7C:
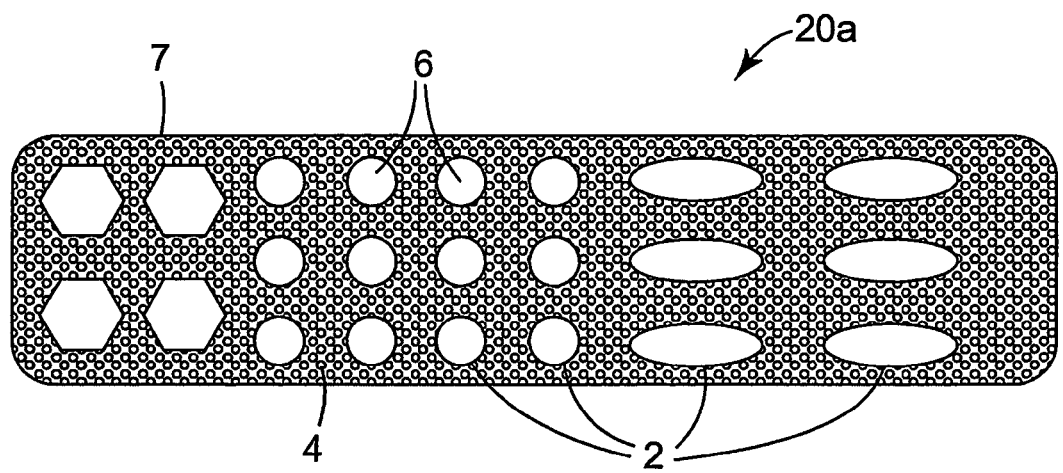

FIG. 7c is a schematic top view of a specific embodiment of a sanitary napkin 20a where the backing 7 covers all of the back sheet 22 of the sanitary napkin. The back sheet 22 is beneath the backing 7 and therefore cannot be seen in FIG. 7c. The through-holes 2 exhibit different geometries along the extension of the back sheet 22 in MD to provide a variation of the bonding mechanism to a fibrous substrate 32 (not shown in FIG. 7c) along such direction.

The present invention will now be further illustrated by the following Examples which are intended to illustrate the invention without limiting it Test Methods 90° Peel Adhesion The 90° peel adhesion was measured according to ASTM D 3330 F using a roll-down weight of 5,000 g.

Hang Shear Adhesion

A sample of the fibrous material 32 against which the fastening film system 1 or the assembly 40, respectively, of the present invention was to be tested, was mounted onto a steel plate with a double-coated adhesive tape. A 40 mm×50 mm piece of the fastening film system 1 or the assembly 40, respectively, was placed with its exposed surface 3a of the backing 7 comprising the male fastening elements 4, onto the fibrous material 32 and rolled down in one cycle using a roll-down hard rubber roll of 5,000 g at a speed of 30.5 cm/min. The dimensions of the sample of the fibrous material 32 exceeded those of said piece of the fastening film system 1 or the assembly 40, respectively, so that all of the exposed surface of such piece was contacting the sample of the fibrous material 32. The resulting construction comprising the fastening film system 1 or the assembly 40, respectively, and the fibrous material substrate 32 was clamped at one end and hung vertically for 15 minutes after which a 100 g weight was attached to the loose bottom end of the resulting construction, generating a shear load at an 180° angle. The time that it took in minutes for the weight to drop at room temperature was recorded as a measure of the hang shear adhesion.

Static Friction

The static friction was measured according to DIN 53375. A piece of the fastening film system 1 or the assembly 40, respectively, was mounted onto a sledge with the surface 3a of the backing 7 being exposed, and placed against a sample of the fibrous material 32 to be tested. The sledge was then pulled with a constant speed of 10 cm/min into a direction within the interfacial area (i.e. normal to the surface vector of the exposed surface 3a of the backing 7) between the fibrous material 32 and the exposed surface 3a of the backing 7 of the fastening film system 1.

EXAMPLES

Example 1

A portion of a mushroom-type hook web which is commercially available under the trade designation 3M Microreplicated Hook CS-600 from 3M Company, St Paul, Minn., USA, was provided. The portion had the dimension of 40 mm in CD and of 50 mm in MD. The thickness of the hook web including the height of the hook male fastening elements 4 was 396 μm. The average height of the hook male fastening elements 4 was about 310 μm. The hook male fastening elements 4 were integral with the backing 7 of the hook web, and they were distributed essentially homogenously across the surface area of the hook web at a density of 1,626 hooks/inch$^2$. The single hook male fastening elements had a stem 4a with a diameter of about 250 μm and an enlarged, oval-shaped portion 4b at the end of the stems opposite to the backing 7 of the hook web.

Circular through-holes 2 were inserted into the portion of the hook by punching whereby the through-holes 2 extended normal to and throughout the backing 7 of the hook web. The circular through-holes 2 each had a diameter of 10 mm.

The hook web thus prepared was then laminated onto a PP film substrate 5 bearing a polystyrene-polyisoprene block-copolymer pressure-sensitive adhesive layer with a thickness of about 35 μm.

The distance between the through-holes 2 was approximately between 1 and 15 mm and was varied to give different ratios of the exposed adhesive area (=surface area of through-holes 2) over the surface area of backing 7 (including the surface area of the through-holes 2) of 0.2, 0.4 and 0.6. For comparative purposes, the ratios of the exposed adhesive area over the surface area of the backing 7 of 0 (=hook web comprising no holes) and 1 (no hook web, only exposed adhesive layer) were tested as well.

A sample of a 100% cotton fabric (=fibrous material 32) having dimensions exceeding the dimensions of the piece of assembly 40 obtained above, was cut from a piece of plain commercial women's undergarment The sample was washed once and had a total weight of 195 g/m$^2$ after washing.

Another sample of a nylon/Elasthan™ fabric (96% nylon, 4% Elasthan) having dimensions exceeding the dimensions of the piece of the assembly 40 obtained above, was cut from a piece of a plain commercial women's undergarment. The sample was washed once and had a total weight of 170 g/m$^2$ after washing.

The samples of the cotton fabric and the nylon/Elasthan fabric were rolled down on the portion of the assembly 40 and, for purposes of comparison, to the hook web and the pure adhesive layer 6, respectively, as described above using a roll down weight of 5 kg.

The results are summarized in Table 1 below and shown graphically in FIG. 4.

TABLE 1

| Ratio of the surface area of through-holes 2 over the surface area of backing 7 | Average 90° peel adhesion [N/40 mm] | | Average hang shear adhesion [min/40 mm × 50 mm] | |
| --- | --- | --- | --- | --- |
| | Cotton | Nylon/Elasthan | Cotton | Nylon/Elasthan |
| 0 | 0.3 | 6.0 | >1,200 | >1,200 |
| 0.2 | 0.4 | 4.1 | >1,200 | >1,200 |
| 0.4 | 0.8 | 3.1 | >1,200 | >1,200 |
| 0.6 | 2.0 | 2.6 | >1,200 | >1,200 |
| 1.0 | 6.5 | 7.4 | >1,200 | >1,200 |

It can be seen from table 1 and the graphical representation in FIG. 4 that the assembly 40 obtained in Example 1 exhibits a well-balanced ratio of an adhesive and mechanical bonding mechanism with respect to both the cotton fabric and the nylon/Elasthan fabric over a broad range of the ratio of the exposed surface area of through-holes 2 (=adhesive area) over the surface area of the backing 7 (=area of the backing 7 including the surface area of through-holes 2). Such ratio preferably is between 0.5 and 0.7. The assembly 40 of Example 1 is therefore suitable for use with different fibrous materials 32 having different total weights of 170 and 195 g/m$^2$, respectively.

Example 2

Example 1 was repeated for a ratio of the surface area of through-holes 2 over the surface area of the backing 7 of 0.2 with the difference that the through-holes 2 had a diameter of 5 mm. The distance of the through-holes 2 was approx. 5 mm. All other parameters and conditions were identical to those of Example 1.

The results are shown in Table 2.

TABLE 2

| Ratio of the surface area of through-holes 2 over the surface area of backing 7 | Average 90° peel adhesion [N/40 mm] | | Average hang shear adhesion [min/40 mm × 50 mm] | |
|---|---|---|---|---|
| | Cotton | Nylon/Elasthan | Cotton | Nylon/Elasthan |
| 0.2 | 0.4 | 3.7 | >1,200 | >1,200 |

Example 3

Example 1 was repeated with the difference that another hook web which is commercially available under the trade designation CS-1010 from 3M Company, St. Paul, Minn., USA, was used. The thickness of the hook web including the height of the hook male fastening elements 4 was 575 μm. The average height of the hook male fastening elements 4 was about 446 μm. The hooks 4 were integral with the backing 7 of the hook web, and they were distributed essentially homogenously across the surface area of the hook web at a density of 490 hooks/inch$^2$. The single hook male fastening element 4 had a stem 4a with a diameter in CD of about 238 μm and a diameter in MD of about 360 μm and an enlarged, anchor-shaped portion 4b having two protrusions emanating from the stem and bending downwards, at the end of the stems opposite to the backing 7 of the hook web. All other parameters and conditions were identical to those used in Example 1.

The results are summarized in table 3 and plotted in FIG. 5.

TABLE 3

| Ratio of the surface area of through-holes 2 over the surface area of backing 7 | Average 90° peel adhesion [N/40 mm] | | Average hang shear adhesion [min/40 mm × 50 mm] | |
|---|---|---|---|---|
| | Cotton | Nylon/Elasthan | Cotton | Nylon/Elasthan |
| 0 | 0.3 | 6.0 | 0 | >1,200 |
| 0.2 | 0.3 | 1.7 | >1,200 | >1,200 |
| 0.4 | 0.9 | 1.6 | >1,200 | >1,200 |
| 0.6 | 1.2 | 1.2 | >1,200 | >1,200 |
| 1.0 | 6.5 | 7.4 | >1,200 | >1,200 |

It can be seen from table 3 and the graphical representation in FIG. 5 that the assembly 40 obtained in Example 3 exhibits a well-balanced ratio of an adhesive bonding mechanism with respect to both the cotton fabric and the nylon/Elasthan fabric over a broad range of the ratio of the surface area of through-holes 2 (=exposed adhesive area) over the surface area of the backing 7 (=area of backing 7 including the surface area of through-holes 2). Such ratio preferably is between 0.4 and 0.9. The assembly 40 of Example 3 is therefore suitable for use with different fibrous materials 32 having different total weights of 170 and 195 g/m$^2$, respectively.

Example 4

Example 1 was repeated using a stem web instead of the hook web. The stem web which was made according to the teaching of Example 1 of U.S. Pat. No. 4,959,268 comprises single stem male fastening elements 4 having a stem 4a with a diameter of about 215 μm but no enlarged portion at the end of the stems. The thickness of the stem web including the height of the stems 4a was about 520 μm. The average height of the stems was about 430 μm. The stems 4a were integral with the backing 7 of the stem web, and they were distributed essentially homogenously across the surface of the stem web at a density of 1,600 stems/inch$^2$.

All other parameters and conditions were identical to those used in Example 1.

The results are summarized in Table 4.

TABLE 4

| Ratio of the surface area of through-holes 2 over the surface area of backing 7 | Average 90° peel adhesion [N/40 mm] | | Average hang shear adhesion [min/40 mm × 50 mm] | | Static friction [mm] |
|---|---|---|---|---|---|
| | Cotton | Nylon/Elasthan | Cotton | Nylon/Elasthan | Nylon/Elasthan |
| 0 | 0 | 0 | | 0 | * |
| 0.2 | 0.5 | >0.3 | >1,200 | | n.m. ** |
| 0.4 | 1.0 | >0.8 | >1,200 | | n.m. ** |

\* the stem web mounted onto the sledge used in DIN 53375 for measuring the static friction was pushed at its front side (i.e. opposite to the side onto which the force was acting) so deep into the fibrous material 32 that the opposite side lost contact to the fibrous material 32 so that meaningful values could not be measured; the sledge did not move initially at all and was then pulled away from any contact with the fibrous material 32 when continuing to move the sledge along with a constant velocity of cm/min
\*\* not measured It can be seen from table 4 that the unmodified stem web backing 7 comprising no through-holes 2 did not exhibit a 90° peel adhesion or a hang shear adhesion with respect to a fibrous cotton or nylon/Elasthan material 32, respectively. The stem-type male fastening elements 4 mechanically interact, however, with the fibrous material 32 as can be seen from the static friction measurements. When introducing through-holes 2 into the stem web backing 7 an adhesive bonding mechanism is present as can be seen from the 90° peel adhesion and hang shear adhesion values for a ratio of the surface area of through-holes 2 (=exposed adhesive surface area) over the surface area of the backing 7 (=area of the backing 7 including the surface area of through-holes 2) of 0.2 and 0.4.

Comparative Examples 1-3

Sanitary napkins commercially available from Procter & Gamble under the trade designation "Always Ultra-normal", from Hartmann under the trade designation "Ria Pantiliners light, air-active" and from Schlecker under the trade designation "AS Classic" were obtained. The garment side of these sanitary napkins comprised an adhesive layer, either arranged in a single strip or in two narrower strips separated by an uncoated area.

The cotton sample and the nylon/Elasthan sample described in Example 1 were attached to such commercially available sanitary napkins using a roll down weight of 5 kg.

The 90° peel adhesion and the hang shear adhesion were measured as indicated in the test method section above.

The results are summarized in table 5 below.

TABLE 5

| Sanitary napkin type | Average 90° peel adhesion [N/40 mm] | | Average hang shear adhesion [min/40 mm × 50 mm] | |
| --- | --- | --- | --- | --- |
| | Cotton | Nylon/Elasthan | Cotton | Nylon/Elasthan |
| Always Ultra-normal | 1.1 | 0.6 | 8 | 42 |
| Ria Pantiliners light, air-active | 0.6 | 0.2 | 6 | 1 |
| AS Classic | 1.5 | 0.4 | 25 | 25 |

Example 5 and Comparative Example 4

Example 1 was repeated for a ratio of the area of through-holes 2 (=exposed adhesive surface) over the surface area of the backing 7 of 0.2, 0.4 or 0.6 using through-holes 2 with a diameter of 10 mm. In a comparative example, the same ratios of 0.2, 0.4 and 0.6 were obtained using a sequence of a first strip of a hook web with no through-holes, a strip with no hook web, i.e. an 8 mm wide strip of the exposed adhesive surface and a second strip of a hook web. The width of theses strips was as follows:

TABLE 6

| Ratio of the surface area of through-holes 2 over the surface area of backing 7 | Width [mm] | | |
| --- | --- | --- | --- |
| | 1st hook strip | adhesive strip | 2nd hook strip |
| 0.2 | 16 | 8 | 16 |
| 0.4 | 12 | 16 | 12 |
| 0.6 | 8 | 24 | 8 |

The results of the measurements are shown in Table 7 below.

TABLE 7

| | Ratio of exposed adhesive surface area over surface area of backing or sum of the surface areas of the hook and adhesive strips | Average 90° peel adhesion [N/40 mm] | |
| --- | --- | --- | --- |
| | | Cotton | Nylon/Elasthan |
| Example 5 (through-holes) | 0.2 | 0.4 | 4.1 |
| | 0.4 | 0.8 | 3.1 |
| | 0.6 | 2.0 | 2.6 |
| Comp. Ex. 4 (strips) | 0.2 | 1.4 | 5.8 |
| | 0.4 | 2.2 | 4.5 |
| | 0.6 | 2.9 | 4.3 |

It can be seen from table 7 that the assemblies 40 of Comparative Example 4 comprising strip-shaped exposed adhesive areas which are not fully encompassed by the backing 7, have distinctly higher average 90° peel adhesion in comparison to the assembly 40 of the invention comprising through-holes 2 with a diameter of 10 mm. The adhesive and mechanical bonding mechanism of an assembly 40 of the invention having a ratio of the surface area of through-holes 2 (=exposed adhesive surface) over the surface area of the backing 7 (=area of backing 7 including the surface area of the through-holes 2) of 0.6, is characterized by an advantageous 90° peel adhesion value to both a cotton based surface and to a nylon based surface which is highly preferable. Such an optimised performance cannot be obtained with the strip-shaped adhesive and mechanical bonding elements.

I claim:

1. Fastening film system comprising a backing and an adhesive layer on one of the two major surfaces of the backing, the backing bearing on its exposed major surface opposite to the adhesive layer a plurality of male fastening elements capable of engaging with fibrous materials 32 having a plurality of complementary female fastening elements, and a plurality of through-holes extending through the thickness of the backing so that the adhesive layer attached to the backing is exposed through such through-holes 2 wherein at least one of said through-holes is encompassed by the backing, and wherein the fastening film system releasably adheres to said fibrous materials through a combination of a mechanical and an adhesive bonding mechanism.

2. A fastening film system according to claim 1 wherein a ratio of the surface area of the through-holes over the surface area of the backing including the surface area of the through-holes is between 15% and 85%.

3. A fastening film system 1 according to claim 1 wherein the average maximum effective extension of the through-holes is at least 1 mm.

4. A fastening film system according to claim 1 wherein the average distance between adjacent through-holes is at least 1 mm.

5. A fastening film system according to claim 1 wherein the average thickness of the backing 1 is between 10 μm and 1 mm.

6. A fastening film system according to claim 1 wherein the adhesive is a pressure-sensitive adhesive.

7. A fastening film system according to claim 6 wherein the adhesive exhibits a 90° peel adhesion from a smooth polyethylene surface of between 1 N/inch and 10 N/inch.

8. A fastening film system according to claim 1 wherein the male fastening elements comprise a stem projecting from the exposed major surface of the backing.

9. A fastening film system according to claim 1 wherein the average density of the male fastening elements with respect to the surface area of the backing including the surface area of the through-holes is between $10/cm^2$, and $5,000/cm^2$.

10. A fastening film system according to claim 1 wherein the male fastening elements are selected so that they can be releasably engaged with a fibrous material having an area weight of less than 350 $g/m^2$.

11. An assembly comprising a substrate and the fastening film system of claim 1 with the adhesive layer being arranged between a surface of the substrate and the one major surface of the backing which is opposite to the exposed major surface of the backing bearing the plurality of male fastening elements.

12. A method of preparing a fastening film system according to claim 1 comprising providing a continuous backing bearing a plurality of male fastening elements, providing a plurality of through-holes extending through the thickness of the continuous backing and laminating the continuous backing onto an adhesive layer.

13. The method according to claim 12 wherein upon providing the plurality of through-holes the continuous backing is subjected to stretching.

14. A method of preparing a fastening film system according to claim 1 comprising providing a continuous backing bearing on a major surface a plurality of male fastening elements; providing one or 2n+1 continuous cuts in a machine direction, with n being an integer, into the continuous backing so that the cut which has a periodic sequence of notches and protrusions characterized by a wavelength and an amplitude forms 2 or 2n adjacent sub-backings; separating the 2 or 2n adjacent sub-backings by about at least the amplitude in a cross-direction and by about half of the wavelength or a multiple of such half of the wavelength in the machine direction: moving the 2 or 2n sub-backings towards each other thereby creating a sequence of through-holes between the 2 or 2n sub-backings; and laminating the sub-backings onto an adhesive layer.

15. A method of preparing an assembly according to claim 11 comprising providing a substrate; applying an adhesive layer to an exposed surface of such substrate; providing a continuous backing bearing on a major surface a plurality of male fastening elements; further providing a plurality of through-holes extending through the thickness of the continuous backing; and attaching the resulting continuous backing comprising through-holes through a major surface opposite to the major surface bearing the plurality of male fastening elements to an exposed surface of the adhesive layer.

16. The method according to claim 15, wherein the continuous backing comprising through-holes is provided by providing one or 2n+1 continuous cuts in a machine direction, with n being an integer, into the continuous backing so that the cut which has a periodic sequence of notches and protrusions characterized by a wavelength and an amplitude forms 2 or 2n adjacent sub-backings; separating the 2 or 2n adjacent sub-backings by about at least the amplitude in a cross-direction and by about half of the wavelength or a multiple of such half of the wavelength in the machine direction; and moving the 2 or 2n sub-backings towards each other thereby creating a sequence of through-holes between the 2 or 2n sub-backings.

17. A disposable absorbent article, comprising a liquid-permeable top sheet, a liquid-impermeable back sheet opposite to said top sheet, a liquid-absorbent core between said top sheet and said back sheet, longitudinal edges, a first end region, and a second end region, the absorbent article further comprising a fastening film system according to claim 1 in order to secure said disposable absorbent article to at least one of a body or an undergarment or panties of a person.

18. The disposable absorbent article according to claim 17, wherein the disposable absorbent article is a disposable diaper comprising tape tabs disposed adjacent each longitudinal edge in the first end region, each of said tape tabs comprising the fastening film system, said disposable diaper further comprising a fibrous material in the second end region or on the back sheet capable of mechanically engaging with the male fastening elements of the fastening film system.

19. The disposable absorbent article according to claim 17, wherein the disposable absorbent article is a disposable sanitary napkin bearing the fastening film system on the back sheet.

* * * * *

UNITED STATES PATENT AND TRADEMARK OFFICE
CERTIFICATE OF CORRECTION

PATENT NO.        : 7,407,496 B2
APPLICATION NO.   : 10/557092
DATED             : August 5, 2008
INVENTOR(S)       : Johann F. Petersen It is certified that error appears in the above-identified patent and that said Letters Patent is hereby corrected as shown below:

Column 1
Line 40, delete "6,402,730," and insert in place thereof -- 6,402,730. --.

Column 8
Line 10, delete "FIG. 3a-3d" and insert in place thereof -- FIGS. 3a-3d --.

Column 10
Line 51, delete "nibs" and insert in place thereof -- ribs --.

Line 65, delete "nibs" and insert in place thereof -- ribs --.

Column 11
Line 8, delete "nibs" and insert in place thereof -- ribs --.

Column 12
Lines 9-13, below "the web." delete "The different zones. . .and CD.".

Lines 14-31, below "and CD." delete "One or more. . .20 and 200 g/m$^2$.".

Column 13
Line 63, delete "adhering to" and insert in place thereof -- bearing --.

Column 16
Line 6, delete "FIG. 3a-3d." and insert in place thereof -- FIGS. 3a-3d. --.

Column 17
Line 12, delete "St" and insert in place thereof -- St. --.

UNITED STATES PATENT AND TRADEMARK OFFICE
CERTIFICATE OF CORRECTION

| | |
|---|---|
| PATENT NO. | : 7,407,496 B2 |
| APPLICATION NO. | : 10/557092 |
| DATED | : August 5, 2008 |
| INVENTOR(S) | : Johann F. Petersen |

It is certified that error appears in the above-identified patent and that said Letters Patent is hereby corrected as shown below:

Column 20
Line 31, delete "FIG. 1 b" and insert in place thereof -- FIG. 1b --.

Line 32, delete "FIG. 1 a." and insert in place thereof -- FIG. 1a --.

Column 21
Line 58, before "(not shown)." delete "29".

Column 22
Line 60, after "it" insert -- . --.

Column 23
Line 44, delete "St" and insert in place thereof -- St. --.

Column 24
Line 11, after "undergarment" insert -- . --.

Column 28
Line 8, in Claim 1, after "materials" delete "32."

Line 12, in Claim 1, delete "through-holes 2" and insert in place thereof -- through-holes, --.

Line 21, in Claim 3, after "system" delete "1".

Line 28, in Claim 5, after "backing" delete "1".

UNITED STATES PATENT AND TRADEMARK OFFICE
CERTIFICATE OF CORRECTION

PATENT NO. : 7,407,496 B2
APPLICATION NO. : 10/557092
DATED : August 5, 2008
INVENTOR(S) : Johann F. Petersen It is certified that error appears in the above-identified patent and that said Letters Patent is hereby corrected as shown below:

Column 29
Lines 4-5 (approx.), in Claim 14, delete "direction:" and insert in place thereof
-- direction --.

Column 30
Line 19, in Claim 18, after "material" insert in place thereof -- at least one of --.

Signed and Sealed this

Twenty-third Day of December, 2008

JON W. DUDAS
*Director of the United States Patent and Trademark Office*